(12) United States Patent
Weissman et al.

(10) Patent No.: US 10,017,761 B2
(45) Date of Patent: Jul. 10, 2018

(54) METHODS FOR PREPARING CDNA FROM LOW QUANTITIES OF CELLS

(71) Applicant: Yale University, New Haven, CT (US)

(72) Inventors: Sherman M. Weissman, New Haven, CT (US); Xinghua Pan, Hamden, CT (US)

(73) Assignee: Yale University, New Haven, CT (US)

( * ) Notice: Subject to any disclaimer, the term of this patent is extended or adjusted under 35 U.S.C. 154(b) by 451 days.

(21) Appl. No.: 14/139,612

(22) Filed: Dec. 23, 2013

(65) Prior Publication Data

US 2014/0213485 A1 Jul. 31, 2014

Related U.S. Application Data

(60) Provisional application No. 61/757,424, filed on Jan. 28, 2013.

(51) Int. Cl.
*C12N 15/10* (2006.01)

(52) U.S. Cl.
CPC ..... *C12N 15/1096* (2013.01); *C12N 15/1093* (2013.01)

(58) Field of Classification Search
CPC ..................................................... C12N 15/10
See application file for complete search history.

(56) References Cited

U.S. PATENT DOCUMENTS

| | | | |
|---|---|---|---|
| 2007/0117121 A1* | 5/2007 | Hutchison .......... | C12N 15/1096 435/6.12 |
| 2010/0015602 A1* | 1/2010 | Korfhage ............. | C12Q 1/6806 435/6.18 |
| 2011/0224105 A1* | 9/2011 | Kurn ....................... | C12P 19/34 506/26 |
| 2011/0281736 A1* | 11/2011 | Drmanac ................ | C40B 20/00 506/2 |
| 2014/0004569 A1* | 1/2014 | Lambowitz ........ | C12N 15/1096 435/91.21 |

OTHER PUBLICATIONS

Pan et al., Two Methods for Full-Length RNA Sequencing for Low Quantities of Cells and Single Cells, Proc Natl Acad. Sci, 2012, 110(2), 594-599.*
Pan et al., Supporting Information, 2012, 110(2), 1-9.*
Pan et al., A Procedure for Highly Specific, Sensitive, and Unbiased Whole-Genome Amplification, Proc Natl Acad. Sci, 2008, 105(40), 15499-15504.*
Kang et al., Transcript Amplification From Single Bacterium for Transcriptome Analysis, Genome Research, 21, 925-935.*
Rodrigue et al., Whole Genome Amplification and De Novo Assembly of Single Bacterial Cells, PLoS One, 2009, 4(9), 1-10.*
Adli, et al., "Genomewide Chromatin Maps Derived from Limited Numbers of Hematopoletic Progenitors", Nat Methods, 7(8):615-8 (2010).

Au, et al., "Improving PacBio long read accuracy by short read alignment". PLoS ONE, 7(10):e46679 (2012).
Boon, et al., "Acoustic microstreaming increases the efficiency of reverse transcription reactions comprising single-cell quantities of RNA", Biotechniques., 50(2):116-9 (2011a).
Boon, et al., "Increasing cDNA yields from single-cell quantities of mRNA in standard laboratory reverse transcriptase reactions using acoustic microstreaming", J Vis Exp., 11(53):e3144 (2011b).
Brukner, et al, "Self-priming arrest by modified random oligonucleotides facilitates the quality control of whole genome amplification", Anal Biochem., 39:345-7 (2005).
Gonzalez-Roca, et al., "Accurate expression profiling of very small cell populations", PLoS ONE, 5(12):e14418 (2010).
Hager, et al., "Transcription dynamics", Mol Cell., 35(6):741-53 (2009).
Hashimshony, et al. "CEL-Seq: single-cell RNA-Seq by multiplexed linear amplification", Cell Rep., 2(3):666-73 (2012).
Heuermann, et al., "Modification of the transplex WTA2 amplification product for next generation sequencing", http://www.sigmaaldrich.com/content/dam/sigma-aldrich/docs/Sigma-Aldrich/Posters/1/wta2_next_generation_sequencing.pdf, retrieved from the interned Dec. 3, 2013.
Hutchison, et al., "Single-cell genomics", Nat Biotechnol., 24:657-8 (2006).
Hutchison, et al., "Cell-free cloning using phi29 DNA polymerase", PNAS, 102:17332-6 (2005).
Islam, et al., "Characterization of the single-cell transcriptional landscape by highly multiplex RNA-seq", Genome Res., 21(7):1160-7 (2011).
Kanamori-Katayama, et al., "Unamplified cap analysis of gene expression on a single-molecule sequencer", Genome Res., 21(7):1150-9 (2011).
Kang, et al., "Transcript amplification from single bacterium for transcriptome analysis", Genome Res., 21:925-35 (2011).
Kurimoto, et al., "An improved single-cell cDNA amplification method for efficient high-density oligonucleotide microarray analysis", Nucleic Acids Res., 34(5):e42 (2006).
Lage, et al, "Whole genome analysis of genetic alterations in small DNA samples using hyperbranched strand displacement amplification and array-CGH", Genome Res., 13:294-307 (2003).
Lecault, et al., "Microfluidic single cell analysis: from promise to practice", Curr Opin Chem Biol., 16(3-4):381-90 (2012).
Liu, et al., "Preparation and analysis of cDNA from a small number of hematopoietic cells", Methods Enzymol., 303:45-55 (1999).

(Continued)

*Primary Examiner* — Amy M Bunker
(74) *Attorney, Agent, or Firm* — Pabst Patent Group LLP

(57) ABSTRACT

Methods for preparing cDNA libraries from single and low quantities of cells are disclosed. The methods are based on the principles of multi-strand displacement amplification or semi-random primed polymerase chain reaction. The methods typically include a step of reverse transcription and subsequent amplification of cDNA. The methods can be adapted for preparation of cDNA libraries that are representative of mRNA or whole RNA expressed by the cell or cells. The cDNA is suitable for sequencing or microarray analysis.

20 Claims, 6 Drawing Sheets

(56) References Cited

OTHER PUBLICATIONS

Ma, et al., "In vivo responses of cutaneous C-mechanosensitive neurons in mouse to punctate chemical stimuli that elicit itch and nociceptive sensations in humans", J Neurophysiol., 107(1):357-63 (2012).
Ma, et al., "In vivo visualization and functional characterization of primary somatic neurons", J Neurosci Methods, 191(1):60-5 (2010).
Marcus, et al., "Microfluidic single-cell mRNA isolation and analysis", Anal Chem., 78(9):3084-9 (2006).
Marcy, et al., "Nanoliter reactors improve multiple displacement amplification of genomes from single cells", PLoS Genet., 3:1702-8 (2007).
New England Bio Labs, "Random primer mix", https://www.neb.com/products/s1330-random-primer-mixhttps://www.neb.com/products/s1330-random-primer-mix, retrieved from Internet Dec. 5, 2013.
Ozsolak, et al., "Digital transcriptome profiling from attomole-level RNA samples", Genome Res. 20(4):519-25 (2010).
Pan, et al., "A procedure for highly specific, sensitive, and unbiased whole-genome amplification", PNAS, 105(40):15499-504 (2008).
Pan, et al., "Two methods for full-length RNA sequencing for low quanities of cells and single cells", PNAS, 110(2):595-9 (2013).
Phillips, et al., "Antisense RNA Amplification: A Linear Amplification Method for Analyzing the mRNA Population from Single Living Cells", Methods, 10(3):283-8 (1996).
Qiagen, "Amazing gene expression and regulation, real-time PCR", Jul. 2010.
Qiu, et al., "Single-neuron RNA-Seq: technical feasibility and reproducibility", Front Genet. 3:124 (2012).
QuantiTect, Whole Transcriptome Kit, http://www.qiagen.com/products/catalog/assay-technologies/real-time-pcr-and-rt-pcr-reagents/quantitect-whole-transcriptome-kit, pp. 1-2, retrieved from the Internet Dec. 5, 2013.
Quantitect, "Whole transcriptome handbook", simple and assay technologies, pp. 1-28 (2011).
Ramsköld, et al., "Full-Length mRNA-Seq from single cell levels of RNA and individual circulating tumor cells", Nat Biotechnol., 30(8):777-82 (2012).
RNeasy Plus Micro (catalog No. 74034; Qiagen), Handbook pp. 1-52 (2007).
Spits, et al., "Whole-genome multiple displacement amplification from single cells", Nat Protoc., 1:1965-70 (2006).
Suter, et al., "Origins and consequences of transcriptional discontinuity", Curr Opin Cell Biol., 23(6):657-62 (2011).
Tang, et al., "mRNA-Seq whole-transcriptome analysis of a single cell", Nat Methods, 6(5):377-82 (2009).
Transplex Whole Transcriptome Amplification or WTA, from Sigma-Aldrich, http://www.sigmaaldrich.com/content/dam/sigma-aldrich/docs/Sigma-Aldrich/Posters/1/wta2_next_generation_sequencing.pdf, pp. 1-2retrieved from the internet Dec. 5, 2013.
Trapnell, et al., "Differential gene and transcript expression analysis of RNA-seq experiments with TopHat and Cufflinks", Nat Protoc., 7(3):562-78 (2012).
Voss, et al., "Dynamic exchange at regulatory elements during chromatin remodeling underlies assisted loading mechanism", Cell, 146(4):544-54 (2011).
Wang, et al., "Alternative isoform regulation in human tissue transcriptomes", Nature, 456(7221):470-6 (2008).
Wang, et al., "Balanced-PCR amplification allows unbiased identification of genomic copy changes in minute cell and tissue samples", Nucleic Acids Res., 32:e76. (2004).
Wang, et al., Single cell analysis: the new frontier in 'omics', Trends Biotechnol., 28(6):281-90 (2010).
Wikipedia, Multiple displacement amplification, http://en.wikipedia.org/wiki/Multiple_displacement_amplification, pp. 1-5, retrieved from the internet Dec. 5, 2013.
Wikipedia, "|29 DNA polymerase", http://en.wikipedia.org/wiki/%CE%A629_DNA_polymerase, pp. 1-9, retrieved from the internet, Dec. 5, 2013.
Zhang, et al, "Sequencing genomes from single cells by polymerase cloning", Nature Biotechnol., 24:680-6 (2006).
Zhong, et al., "A microfluidic processor for gene expression profiling of single human embryonic stem cells ", Lab Chip. 8(1):68-74 (2008).
Zhu, et al., "Reverse transcriptase template switching: a SMART approach for full-length cDNA library construction", Biotechniques., 30(4):892-7 (2001).

\* cited by examiner

SEQUENCE LISTING

```
<160> NUMBER OF SEQ ID NOS: 5

<210> SEQ ID NO 1
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(26)
<223> OTHER INFORMATION: N = any nucleotide

<400> SEQUENCE: 1
gacatgtatc cggatgtnnn nnnnnn                                        26

<210> SEQ ID NO 2
<211> LENGTH: 32
<212> TYPE: DNA
<213> ORGANISM: Artificial Sequence
<220> FEATURE:
<223> OTHER INFORMATION: Primer

<400> SEQUENCE: 2
gacatgtatc cggatgtttt tttttttttt tt                                 32

<210> SEQ ID NO 3
<211> LENGTH: 17
<212> TYPE: DNA
<213> ORGANISM: Artificial Sequence
<220> FEATURE:
<223> OTHER INFORMATION: Primer

<400> SEQUENCE: 3
gacatgtatc cggatgt                                                  17

<210> SEQ ID NO 4
<211> LENGTH: 33
<212> TYPE: DNA
<213> ORGANISM: Artificial Sequence
<220> FEATURE:
<223> OTHER INFORMATION: Primer

<400> SEQUENCE: 4
gacatgtatc cggatgtttt tttttttttt ttv                                33

<210> SEQ ID NO 5
<211> LENGTH: 34
```

```
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (34)..(34)
<223> OTHER INFORMATION: N = any nucleotide

<400> SEQUENCE: 5
gacatgtatc cggatgtttt ttttttttt ttvn                                    34
```

METHODS FOR PREPARING CDNA FROM LOW QUANTITIES OF CELLS

CROSS-REFERENCE TO RELATED APPLICATIONS

This application claims the benefit of and priority to U.S. Ser. No. 61/757,424 filed Jan. 28, 2013 and which is incorporated by reference in its entirety.

The Sequence Listing submitted Mar. 24, 2014 as a text file named "YU_5976_ST25.txt," created on Mar. 18, 2014, and having a size of 1,331 bytes is hereby incorporated by reference pursuant to 37 C.F.R. § 1.52(e)(5).

STATEMENT REGARDING FEDERALLY SPONSORED RESEARCH

This invention was made with government support under HD066457 and GM099130 awarded by National Institute of Health. The government has certain rights in the invention

FIELD OF THE INVENTION

The invention is generally directed to methods for amplifying cDNA libraries from low quantities of cells and single cells in suitable quantity and quality for transcriptome analysis through sequencing or microarray analysis.

BACKGROUND OF THE INVENTION

Most populations of cells from higher eukaryotes are heterogeneous in ways that cannot be fully elucidated by bulk analysis. The causes of this heterogeneity include: differentiation in subtly different ways, varying stages of the cell cycle, cellular senescence, and non-uniform RNA processing and degradation. Such cellular heterogeneity could be studied by robust techniques for single cell transcriptome analysis, particularly if the techniques analyze full-length transcripts. Reliable methods for transcriptome analysis are also required for situations where only low quantities of (LQ) cells are available, and where the RNA may be partly degraded.

Advances in high throughput sequencing and innovations in biochemical techniques have revealed a complex picture of the mammalian transcriptome (Wang, et al., *Nat Rev Genet.* 10(0:57-63 (2009)). Most genes that contain three or more exons give rise to alternatively spliced products that may vary with the cell type or state of differentiation (Wang, et al., *Nature* 456(7220:470-476 (2008)), and these alternative splice forms often have different, even antagonistic functions. In an extreme case, the *Drosophila* Dscam gene has >30,000 alternative transcripts hypothesized to provide distinct identities to individual neuronal dendrites, and avoid self interaction between the processes of a single neuron (Hattori, et al, *Nature* 461(7264):644-648 (2009)). Thousands of long, polyadenylated, intergenic "non-coding" RNAs (LINCs) have been discovered (Guttman, et al., *Nature* 458(7235):223-227 (2009), Carninci, *DNA Res.* 17(2):51-59 (2010)) that may have diverse regulatory functions, including serving as scaffolds for proteins that interact with chromatin (Khalil, et al., *Proc Natl Acad Sci USA* 106(28):11667-11672 (2009)). A fraction of these LINC RNAs may be translated, and encode short peptides (Ingolia, et al., *Science* 324(5924):218-223 (2009)). Cytoplasmic recapping of RNAs has been demonstrated enzymatically (Schoenberg, et al., *Trends Biochem Sci.* 34(9):435-442 (2009), Otsuka, et al., *Mol Cell Biol.* 29(8):2155-2167 (2009)). A number of genes use multiple promoters, and the position of the 5' transcription start sites of RNAs may shift under different physiologic conditions. Finally, the mRNA 5' "untranslated (UTR)" regions are now known to be translated frequently (Brar, et al., *Science* 335(6068):552-557 (2012) Oyama, et al., *Mol Cell Proteomics* 6(6):1000-1006 (2007) Oyama, et al., *Genome Res.* 14(10B):2048-2052 (2004)), and may produce biologically active peptides. More than half of the translation initiation sites used by a cell are not predicted from annotated genes. These new sites include many that occur in the 5' leader sequences of mRNAs, and may use near-canonical UUG, CUG, or GUG start codons. Hundreds of genes also show internal translation starts (Ingolia, et al., *Cell.* 147(4):789-802 (2011)). These could generate proteins with altered functions (Wethmar, et al., *Bioessays.* 32(10):885-893 (2010)). These complications, as well as issues such as RNA editing and allele specific levels of expression (Pastinen, *Nat. Rev.* 11(8):533-538 (2010)), all indicate the value of deep sequencing of full length transcripts.

Several approaches have been proposed for obtaining transcriptome data from single cells. A pioneer approach used reverse transcriptase and oligo-dT primers with a T7 phage RNA polymerase promoter sequence attached to the 5' end of the oligo-dT run. The resulting cDNA was transcribed into multiple copies of RNA which were then converted back to cDNA (Phillips, et al., *Methods* 10(3): 283-288 (1996)). This often truncates the cDNA molecule, losing 5' sequences of the original mRNA, especially for relatively long transcripts, and requires multiple rounds of processing when starting with LQ cells, further exacerbating cDNA truncation. A recent modification (Hashimshony, et al., *Cell Rep.* 2(3):666-673 (2012)) enables multiplex analyses, but this is still 3' end sequence biased. Other methods are based on PCR amplification of cDNA (Liu, et al., *Methods Enzymol.* 303:45-55 (1999), Ozsolak, et al., *Genome Res.* 20(4):519-525 (2010), Gonzalez, et al., *PLoS ONE.* 5(12):e14418 (2010), Kanamori, et al., *Genome Res.* 21(7):1150-1159 (2011), Islam, et al., *Genome Res.* 21(7): 1160-1167 (2011), Tang, et al., *Nat. Methods.* 6(5):377-382 (2009), Kurimoto, et al., *Nucleic Acids Res.* 34(5):e42 (2006), Qiu S, et al., *Front Genet.* 3:124 (2012)).

However, these approaches may yield biased representations of sequences along the mRNA, and fail to give complete sequences for long mRNAs because long DNA templates are discriminated against even when a long PCR reaction is used. The Smart-Seq method (Ramsköld, et al., *Nat Biotechnol.* 30(8):777-782 (2012)) has been reported to use a long PCR method that provided sequences for a substantial portion of even very long cDNAs, although the distribution of sequences was uneven and the sequences of the 5' regions of many mRNAs were depleted.

In view of short falls, there remains a need for improved ways of obtaining transcriptome data from single cells.

Therefore, it is an object of the invention to provide methods of amplifying cDNA from RNA isolated from low quantities of cells and single cells.

It is a further object of the invention to provide methods for full-length RNA (cDNA) sequencing for low quantities of cells and single cells.

It is another object of the invention to employ the methods of full-length RNA sequencing in diagnostic assays.

It is another object of the invention to employ the methods of in assays designed to test drug or other treatment efficacies.

SUMMARY OF THE INVENTION

Methods of preparing cDNA libraries suitable for transcriptome analysis are disclosed. In some embodiments, the methods rely on the principles of multi-strand displacement amplification (MDA). An example of such a method can include a reverse transcription (RT) reaction including denaturing RNA; annealing one or more RT primers to the RNA; and extending the RT primers to form single stranded cDNA. Optionally, double stranded cDNA can be prepared by second strand synthesis of the single stranded cDNA. Next, the cDNA is circularized and amplified by a multiple displacement amplification (MDA) reaction including annealing one or more MDA primers to the cDNA and extending the MDA primers with a phi29 DNA polymerase to form the cDNA library.

Typically, the RT primers are single stranded oligonucleotides such as 5'-phosphorylated oligo(dT); 5'-phosphorylated oligo(dT) with a 3' anchor nucleotide that is not thymidine; a mixture of random primers; or any combination thereof. If oligo(dT) primers are used for RT, the cDNA library will be representative of expressed mRNA. If random primers are used for RT alone or in combination with oligo(dT) primers, the cDNA library will be representative of total expressed RNA. In a particularly embodiment, the whole MDA reaction is carried out for at least 4 hours at a temperature between about 28° C. to 30° C. the presence of Tre[d-(+)-trehalose dehydrate] at a concentration of 0.2M to 1M, for example, between 0.54-0.84 M. Optionally, the MDA reaction can also be carried out for a short time, as quick as 1-2 hours, without Trehalose.

An alternative method relies on the principles of semi-random primed PCR. Such a method can include a reverse transcription (RT) reaction including denaturing RNA; annealing one or more RT primers to the RNA; and extending the RT primers to form the cDNA. Second strand synthesis is optional. Next, cDNA is amplified by a semi-random primed polymerase chain reaction procedure including two steps. In a first step a cDNA library uniformly covering all cDNA sequences is generated as relatively short-sizes of constructs each flanked by a universal sequence. In the second step the library is amplified by polymerase chain reaction (PCR).

The first step typically includes denaturing the cDNA, annealing a semi-random primer to the cDNA, and extending the semi-random primer with a DNA polymerase. The semi-random primer is actually a mixture of primers including a universal 5' sequence capable for self-annealing into a hairpin or hairpin loop structure, and a 3' sequence including a random N stretch wherein "N" can be any nucleotide which allows the primer to uniformly amplify full length cDNA sequences of all transcripts during PCR. Typically, the primer includes restriction sequences that allow the universal primer sequences to be removed from the cDNA by restriction digestion after PCR.

In a second step the library is amplified by PCR using the universal sequence on the two ends of the constructs as priming sites. This includes multiple cycles of denaturing, annealing, and extending the PCR primer to form a final cDNA library.

Typically, the primers for RT primers for this method are also single stranded oligonucleotides with a sequence consisting of oligo(dT); oligo(dT) with a 3' anchor nucleotide that is not thymidine; a mixture of random primers; and any combination thereof. Preferably, the oligo(dT) primer, the random primer, or a combination thereof further includes a 5' sequence capable for self-annealing into a hairpin or hairpin loop structure. The 3' sequence of the random primer includes a random N stretch wherein "N" can be any nucleotide. The RT primers can also include a universal primer sequence as discussed above for the semi-random primer. The random primer, and optionally the oligo(dT) primer, or any combination thereof can include a sequence that can be cut by a restriction endonuclease to remove the universal primer sequence from the amplified cDNA. Therefore, in some embodiments one of the RT primers is the same as the semi-random primer. In a particular embodiment, the semi-random primer and/or at least one of the RT primers includes the sequence 5'-GACATGTATCCGGATGTNNNNNNNNN-3' (SEQ ID NO:1) and the PCR primer includes the sequence 5'-GACATGTATCCGGATGT-3' (SEQ ID NO:3).

The methods can be further modified to enhance RNA collection, cDNA amplification or minimize contamination. For example, cellular RNA can be prepared by lysing cells under conditions that disrupt the plasma membrane of the cells but do not disrupt the nuclear membrane of the cells.

Optional steps include substantially purifying the RNA or cDNA from contaminates such as genomic DNA, reaction enzymes, and unused primer.

Additional steps can include fragmenting the cDNA library to achieve certain sized fragments suitable for subsequence analysis (e.g., 150-500 base pairs). In some embodiments, adaptor oligonucleotides are ligated to the cDNA to facilitate sequencing.

Methods of using the cDNA libraries for subsequent transcriptome analysis, for example sequencing or microarray, are also provided.

DETAILED DESCRIPTION OF THE INVENTION

I. Definition

Figure 1A:
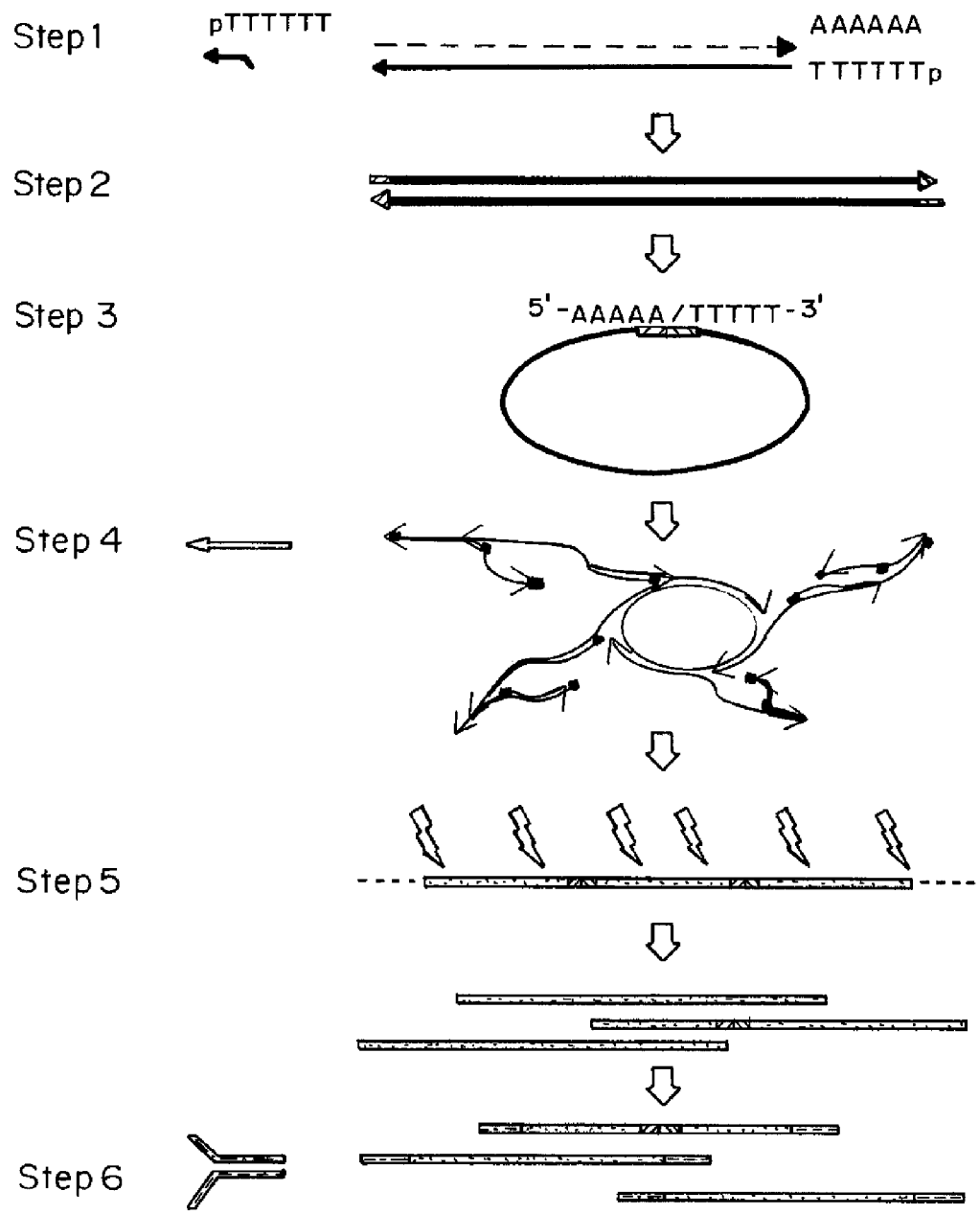
FIGS. 1A-1D are diagrams illustrating steps of exemplary Phi29 DNA Polymerase-Based mRNA Transcriptome Amplification (PMA) (FIG. 1A), Semirandom Primed PCR-Based mRNA Transcriptome Amplification (SMA) (FIG. 1B), Phi29 DNA Polymerase-Based Whole Transcriptome Amplification (PTA) (FIG. 1C), and Semirandom Primed PCR-Based Whole Transcriptome Amplification (STA) methods.

"Isolated," "isolating," "purified," "purifying," "enriched," and "enriching," when used with respect to nucleic acids of interest, indicate that the nucleic acids of interest at some point in time were separated, enriched, sorted, etc., from or with respect to other cellular material to yield a higher proportion of the nucleic acids of interest compared to the other cellular material, contaminates, or active agents such as enzymes. "Highly purified," "highly enriched," and "highly isolated," when used with respect to nucleic acids of interest, indicates that the nucleic acids of interest are at least about 70%, about 75%, about 80%, about 85%, about 90% or more, about 95%, about 99% or 99.9% or more purified or isolated from other cellular materials, contaminates, or active agents such as enzymes. "Substantially isolated," "substantially purified," and "substantially enriched," when used with respect to nucleic acids of interest, indicate that the nucleic acids of interest are at least about 70%, about 75%, or about 80%, more usually at least 85% or 90%, and sometimes at least 95% or more, for example, 95%, 96%, and up to 100% purified or isolated from other cellular materials, contaminates, or active agents such as enzymes.

II. Methods of Making cDNA Libraries

The ability to determine the gene expression pattern in low quantities of cells or single cells is important for resolving a variety of problems in many biological disciplines. A robust description of the expression signature of a single cell requires determination of the full-length sequence of the expressed mRNAs in the cell, yet existing methods are typically characterized by a 3' biased or variable transcript representation.

Improved methods for preparing cDNA libraries from low qualities are disclosed. As discussed in more detail below, the procedures utilize either phi29 DNA polymerase-based DNA amplification or semi-random primed PCR amplification of cDNA generated by reverse transcription with oligo-dT and/or random oligonucleotide primers. Unlike existing methods, these protocols produce relatively uniformly distributed sequences covering the full length of almost all transcripts independent of their sizes, and are effective for detection/coverage of the relative abundant mRNAs from as few as a single cell. The uniform amplification that results for the methods described herein typically provides a more complete representation of the transcriptome than existing methods.

Methods for preparing total cellular RNA, first and second strand synthesis of cDNA, and amplification of cDNA to form cDNA libraries are described below. Each of the methods provides guidance for reaction reagents and conditions such as temperature and length of time. It will be appreciated that each the methods can be modified to include alternative, fewer, or additional reaction buffers or components, higher or low reaction temperatures, short or longer reaction times, modified order of reactions, alternative reaction volumes, or combinations thereof. For example, in some embodiments, the temperature or length of a thermal cycle is varied by increasing or decreasing the temperature by 1, 2, 3, 4, 5, 6, 7, or more degrees, or by increasing or decreasing the reaction duration by 1, 2, 3, 4, 5, 6, 7, 8, 9, 10, 15, 30, or more seconds or minutes, or hours (e.g., the time for phi29-polymerase-based amplification).

The methods disclosed herein are capable of preparing representative transcriptomes of single and low quantities of cells. Therefore, in some embodiments, the number of starting cells are less than 100,000, less than 10,000, less than 1,000, less than 100, less than 10, or 1. The cells can be eukaryotic or prokaryotic.

A. Preparation of Total RNA

The disclosed methods can be used to prepare cDNA libraries that are representative the total RNA or mRNA present in the cell or cells from which the RNA starting material is prepared. Typically, RNA starting materials is accessed by lysing or otherwise disrupting one or more cells of interest under conditions that prevent loss or degradation of RNA. For example, the conditions or buffers used can include reagents (e.g., inhibitors) be carried out under conditions that reduce or inhibit the activity of RNase.

Preferably the RNA starting material is separated from genomic DNA. In some embodiments, the RNA is isolated from the cell lysate for uses in the subsequent steps of the cDNA library preparation. In some embodiments, the genomic DNA is removed from the cell lysate, and the cell lysate, including total cellular mRNA is utilized as the starting material for reverse transcription. In some embodiments, isolation of total RNA and removal of genomic DNA are combined.

Methods and kits for facilitating RNA isolation, and/or removal of genomic DNA are known in the art and can be used or modified as discussed herein to facilitate preparation of RNA for reverse transcription. An exemplary kit is RNeasy® Plus Micro Kit (Qiagen). The process typically includes spinning cell or tissue lysates through spin columns to remove genomic DNA. Next, total RNA is purified using a second spin column. In a preferred embodiment, an RNA carrier, such synthetic poly(A) RNA, can added to the lysis buffer before homogenizing the cells. The Examples below show that using this modified protocol, RNA can be eluted with 14 μL 0.1×TE, to obtain approximately 12 μL RNA.

The cells are lysed under mild conditions that breakdown the cell's plasma membrane, but leave the nuclear membrane substantially or completely intact. In this way starting, cytoplasmic RNA can be more easily and completely harvested from the genomic DNA that can contaminate or otherwise corrupt preparation of cDNA library. In this way the column purification is of RNA is prevented and consequently the RNA included with the cytoplasm can be more efficiently recovered. The RNA harvested in this are enriched for cytoplasmic RNA relative to nuclear RNA. The methods can include a centrifugation sequence wherein the supernatant containing cytoplasmic RNA is recovered for RT.

Mild lysis buffer can include one or more detergents such as TRIXTON®-X100, IGEPAL CA-630, NP40, TWEEN® 20 at a concentration of about 0.01 to about 2%. Buffer can include TCEP (tris(2-carboxyethyl)phosphine). The lysis can be carried out are room temperature, or for a shorter period of time at warmer temperature. The lysis is typically carried out for between about 10 minutes and 2 hours at a temperature between about 4° C. and 75° C. A DNA endonuclease can be applied to digest the genomic DNA, and the RNA retained and used for RT.

In a particular embodiment, the cell or cells collect at about 0.5 to 1 microliter volume PBS are disrupted in a cytoplasm lysis buffer (3 microliter) including (final concentration) TRIXTON®-X100×0.5%, NaCl×20 mM, EDTA×0.5 mM, plus fresh added RNaseOut plus DTT or RNase Inhibit (<10% volume). The TRIXTON®-X100 can be replaced by IGEPAL CA-630, or NP40, or TWEEN20®. This lysis reaction is performed at room temperature for 10 minutes, pipetting, finger flip, or agitating etc., is applied to promote the lysis. After this process, the sample is spun down at 10000 rpm×5 minutes at 4° C., and the supernatant is recovered with pipetman under direct vision, without touching the pellet. And a second recover is applied with water or RT mixture (without reverse transcriptase) and spinning down.

The reverse transcription and optionally cDNA amplification can be carried out without removing genomic DNA or without purifying RNA (and/or cDNA). For example, in some embodiments, a "single tube" protocol is employed wherein cell lysis, reverse transcription, optionally cDNA amplification, and optionally subsequent steps are carrier out in a single tube. In one particular embodiment, the cytoplasm lysis buffer is applied to the cell/cells for 30 minutes at room temperature, without spinning down or transferring the supernatant. Instead DNase I with its buffer is added, and the tube is kept at room temperature for up to 30 more minutes, or 37° C. for 5-10 minutes. The reaction is stopped with 20 mM EDTA and heating at 68° C.×5 minutes. In the subsequent RT reaction, the EDTA is balanced with Magnesium Chloride (1.2 Mg: EDTA=1.2:1 molar). Therefore, one or more of RT and optional second strand synthesis, end-blunting, phosphorylation and ligation, the amplification (e.g., using phi29 DNA polymerase and its related components) can be performed in the same tube. In a particular embodiment, during each step the reaction volume is enlarged (usually doubled) and the buffer is adjusted, without purification until the cDNA amplicon is obtained and the cDNA amplification is completed. In some embodiments, the enzyme(s) are inactivated between one or more of the steps. In some embodiments, none of the enzymes are inactivated.

It is generally understood that as more strict RNA purification is employed there will be less contamination by genomic DNA, but more of the total RNA will also be lost. This can lead to a reduction in low frequency transcripts below what can be suitably amplified as cDNA. Accordingly, in some embodiments, few or no purification steps are employed with the RNA starting material is being prepared from between 1 and 10,000 cells, between 1 and 1,000 cells, between 1 and 500 cells, between 1 and 100 cells, between 1 and 50 cells, between 1 and 10 cells, or 1 cell. Alternatively, in some embodiments, one or more steps of RNA purification or genomic DNA removal are employed when the RNA starting material is being prepared from 1 cell, more preferably between 1 and 10 cells, more preferably between 1 and 50 cells, more preferably between 1 and 100 cells, more preferably between 1 and 500 cells, more preferably greater than 1,000 cells, more preferably greater than 10,000 cells, most preferably greater than 10,000 cells.

B. Reverse Transcription

RNA starting material is used as a template for reverse transcription to prepare a single stranded cDNA. A reverse transcription (RT) reaction refers to the process in which single-stranded RNA is reverse transcribed into complementary DNA (cDNA) by using total cellular RNA or poly(A) RNA, a reverse transcriptase enzyme, one or more primers, dNTPs (refers to a mixture of equal molar of dATP, dTTP, dCTP, and dGTP), and typically an RNase inhibitor. An RT reaction can also be referred to as first strand cDNA synthesis.

1. Reaction Procedure

General methods and kits including reaction components for reverse transcription are known and the art and can be employed in the disclosed methods.

The primer or primers for RT reactions are typically random primers for preparing cDNA of total RNA, and poly d(T) or a combination of random primer and poly d(T) for selectively preparing cDNA of mRNA. Preferred primer and primer combinations are discussed below for each of the disclosed cDNA amplification methods.

A typical reaction mixture includes RNA, primer, dNTP nucleotide mixture, reverse transcriptase, RNase inhibitor, buffer including Tris-HCl, KCl, $MgCl_2$, DTT, and nuclease free water up to the desired reaction volume.

In a typical protocol, RNA is first incubated with a primer under conditions that denature RNA secondary structure (e.g., about 70° C.) and then quickly chill on ice to let the primer anneal to the RNA.

Next, other components of RT are added to the reaction including dNTPs, RNase inhibitor, reverse transcriptase and RT buffer.

A typical extension reaction is carried out under conditions that allow the primer to be extended by reverse transcriptase. A typical reaction is carried out for 15, 30, 45, 60, or more minutes at a temperature between about 37° C. and 55° C. For some thermal insensitive reverse transcriptase enzymes, the reaction can be carried out at higher temperatures. In one embodiment, SuperScript Reverse Transcroptase III (SSRTIII) is used to generate a full length cDNA. Following the annealing and extension reaction, the reverse transcriptase can be inactivated with a short incubation at a high temperature (e.g., 5-10 min at >70° C.). The template RNA can be destroyed by treating the RT reaction with RNase H.

In some embodiments second strand synthesis is carried out to prepare double stranded cDNA for the subsequent cDNA amplification steps described in more detail below. The first strand and the second strand are generated in the same reaction mixture and conditions.

In a particular embodiment, the RT reaction described in the Examples below is employed. Briefly, before the first-strand cDNA (sscDNA) generation, a denaturation and primer annealing step is applied: EDTA (5 mM, which became 3.5 mM in the RT reaction), dNTPs (N=A, T, G, or C, each 0.5 mM in RT), and primer (4 μM in RT) are added to a tube, placed at 70° C. for 5 min, and then immediately moved to a temperature below 0° C.

An RT reaction can be carried out in, for example, in a 20-μL volume, with addition of the first-strand buffer (final 1×: 50 mM Tris-HCl, pH 8.3, 75 mM KCl, and 6 mM $MgCl_2$), $MgCl_2$ (6 mM), DTT (2 mM; Invitrogen), RNase inhibitor (0.8 U/μL), and reverse transcriptase (10 U/μL). A thermal program for RT can be 30° C.×5 min, 37° C.×3 min, 45° C.×3 min, 50° C.×60 min, and 70° C.×10 min, followed by cooling to 4° C. In a particular embodiment, the thermal program does not include one or more of the following steps 30° C.×5 min, 37° C.×3 min, or 45° C.×3 min.

In one specific embodiment, the thermal program consists of a single step: an extension reaction for at least 30 minutes at temperature between 37° C. and 55° C., preferably between about 45° C. and about 52° C., more preferably between 49° C. and 51° C., most preferable 37° C. and 50° C. In the Examples below, 50° C. was selected as the reaction temperature for efficient RT using SSRTIII at temperature that minimizes the effects of RNA secondary structure on cDNA synthesis.

Some embodiments include second strand synthesis. In a particular embodiment, second strand synthesis is generally carried out according to the method discussed in the Examples below. For example, second strand can be generated in a 40-μL reaction on the cDNA product from the RT reaction above, with, or preferably without purification. Accordingly, both reactions can be carried out in the same tube. Additional components for second strand synthesis can include: Second Strand Buffer (0.8× concentration: 16 mM Tris-HCl, 9.6 mM $(NH_4)_2SO4$, 8 mM $MgCl_2$, 0.128 mM β-NAD; NEB), RNaseH (0.1 U/μL; Epicentre), *Escherichia coli* DNA ligase (0.125 U/μL; Epicentre), *E. coli* DNA polymerase (0.15 U/μL), and dNTPs (0.125 mM). The reaction can be processed at 16° C.×120 min, followed by 70° C.×10 min for inactivation of the enzymes.

In some embodiments, the single or double stranded cDNA is purified. Methods and kits from purifying cDNA are known and the art and include, for example, the Genomic DNA Clean and Concentrator kit (Zymo) to remove enzymatic reaction components and other impurities from the cDNA preparation. In an exemplary protocol DNA binding buffer (e.g., ChIP DNA Binding Buffer) is added a sample and then transferred to a spin column that binds that cDNA. The protocol can be modified to added additional carrier RNA, for example synthetic poly(A) RNA, (e.g., 100 ng) to the DNA binding buffer prior to adding the binding buffer to the cDNA preparation. In some other embodiment, for example the "single tube" procedure, no column purification is applied in between the different reactions till the amplicon is obtained.

2. Primer Selection

The methods of cDNA amplification disclosed below can be used to increase the yield and the specificity of the cDNA prepared by an initial RT reaction. The cDNA amplification methods are generally based on the principles of multiple displacement amplification (MDA), or the principles of semi-random primed polymerase chain reaction. Methods based on each of the two principles can be modified to preferentially amplify total cellular RNA (referred to herein as whole transcriptome amplification) or mRNA (mRNA transcriptome amplification) based on the selection of primers used for the RT step discussed below.

a. Primers for mRNA Transcriptome Amplification

Primers for mRNA transcriptome amplification generally rely on the principles of oligo(dT) priming. Oligo(dT) refers to a short single-stranded sequence of deoxythymidine (dT). The primers typically include a stretch of at least 12 thymidines. In reverse transcriptase reactions, the primer binds to the poly(A) tail of mRNA molecules. Therefore, use of oligo(dT) as the only primer during an RT reaction will convert mRNA to cDNA, but will not necessarily convert other cellular RNAs to cDNA. Oligo(dT) always initiates reverse transcription at the 3' end of the transcript resulting in a specific mRNA amplification. However, some difficult RNA secondary structures may lead to incomplete cDNA synthesis. Oligo(dT) priming of fragmented RNA may also be problematic. Employing of SSRTIII at high temperature (for example at 50° C.) after an initial 70° C. denaturation resolve most, if not all, of this problem.

Multiple types of oligo(dT) primers are known in the art and commercially available. For example, Oligo(dT)20 is a homogenous mixture of 20-mer thymidines, while oligo(dT) 12-18 is a mixture of 12-mer to 18-mer thymidines. Therefore, the primers for mRNA transcriptome amplification are typically oligo(dT) primers. The stretch of poly(T) can be any length suitable to hybridize to an mRNA poly(A) tail and be extended by reverse transcriptase during a RT reaction. Typically, the poly(T) stretch is between about 5 and about 30 nucleotides. The primer can also be a mixture of oligo(dT) primers that have poly(T) stretches of different lengths.

In a particular embodiment, the oligo(dT) is an anchored oligo(dT). Anchored oligo(dT) primers are designed to avoid polyA slippage by ensuring that they anneal at the 3'UTR/polyA junction. Choosing the best oligo(dT) primer may depend in part on the temperature of the reverse transcription. More thermostable RTs such as SuperScript® III Reverse Transcriptase may perform better with longer primers, which remain more tightly annealed at elevated temperatures compared to their shorter counterparts.

An anchored oligo(dT) typically includes stretch of poly (T) followed a nucleotide that is not thymidine (expressed as "V" which can adenine, cytosine, or guanine). This primer is used as a mixture so all species of "V" (adenine, cytosine, and guanine) are represented in a mixture. In some embodiments, the non-thymidine nucleotide is the 3' terminal nucleotide. In other embodiments, the "V" nucleotide is followed by one or more additional nucleotides that can be thymidine, adenine, cytosine, or guanine (referred to "N"). This primer is also a mixture so all species of "N" are represented. Oligo(dT) primers can be expressed as Oligo $(dT)_n$, where "n" is the number of thymidines in the poly(T) stretch. Preferably, "n" is any integer between 5 and 30. Anchored Oligo(dT) primers can be expressed as oligo$(dT)_n$V, where "n" is the number of thymidines in the poly(T) stretch and "V" is adenine, cytosine, and guanine, or oligo $(dT)_n$VN, where "n" is the number of thymidines in the poly(T) stretch and "V" is adenine, cytosine, and guanine, and "N" is any nucleotide. In a particular embodiment, when the synthetic polyA RNA carrier is applied, oligo$(dT)_n$V, or oligo$(dT)_n$VN is preferred to reduce reverse transcription of the polyA RNA carrier as the template, and helps avoid polyA RNA-derived RT product.

The oligo(dT) primer can be phosphorylated at the 5' end. This is particularly preferred for the RT step preceding MDA-based cDNA amplification methods discussed below which include a circularization step. This modification allows the cDNA to be a substrate for DNA ligase. Primers and other oligonucleotides can also be chemically synthesized at the 5' end of the oligonucleotide when the oligonucleotide is synthesized. In other embodiments, the primers are not 5' phosphorylated and cDNA is phosphorylated after RT and before circularization. Methods of phosphorylating polynucleotide are known in the art and include, for example, use of a polynucleotide kinase.

In a particular embodiment, the primer for mRNA transcriptome amplification is oligo$(dT)_n$, oligo$(dT)_n$V, 5' phosphorylated oligo$(dT)_n$, or 5' phosphorylated oligo$(dT)_n$V wherein "n" is between 21 and 27, between 22 and 26, between 23 and 25, is 24, or is a mixture of any combination of length thereof.

b. Primers for Whole Transcriptome Amplification

Primers for whole transcriptome amplification generally rely on the principles of random priming. Random primer is a mixture of primers where the sequence is a random mixture of the 4 DNA bases. Random hexamer primer is commonly used in RT reactions. Random hexamer primer is typically a mixture of oligonucleotides, for example, 4096 different primer sequences. Although hexamers are common, the random primer can be more or less nucleotides in length, or a mixture thereof. For example, the random primer can be 5, 6, 7, 8, 9, 10, 11, or 12 nucleotides in length. In a particular embodiment, the random primer is a 9-mer.

As discussed above with respect to oligo(dT) primers, random primers can be phosphorylated at the 5' end. Therefore, a preferred primer for the RT step preceding MDA-based whole transcriptome amplification procedures discussed herein includes use of a 5' phosphorylated random primer.

In preferred embodiment, the RT reaction preceding whole transcriptome cDNA amplification includes an oligo (dT) primer and a random primer. As discussed above oligo(dT) selectively amplifies mRNA. Conversely, random primer only can result in incomplete coverage of the 3' end of transcripts. A mixture of random and oligo(dT) primers increase the uniformity and consistency with which the entire RNA population is covered by RT.

c. Specific Primer Embodiments

The principles, steps, and procedures of MDA-based and semi-random primed PCR cDNA amplification are discussed in more detail below. However, as discussed above, the practitioner must decide which procedure will be employed (MDA-based/mRNA transcriptome; MDA-based/ whole transcriptome; semi-random primed PCR/mRNA transcriptome; or semi-random primed PCR/whole transcriptome) because different primer or primer combinations are selected for RT based on the desired amplification procedure and the desired transcriptome.

Typically both the primer or primers for RT reaction preceding both MDA-based and semi-random primed PCR for mRNA transcriptome amplification are oligo(dT) primers. Preferably, RT preceding MDA-based methods utilizes 5' phosphorylated primer. In some embodiments, the oligo (dT) is anchored. Results show that the anchoring nucleotide can decrease RT efficiency for the synthetic polyA RNA carrier.

Typically, the primer or primers for RT reaction preceding MDA-based whole transcriptome amplification include a random primer or mixture therefore, for example random 9-mer, and are preferably 5' phosphorylated. The RT can also include oligo(dT) primer in combination with random primer.

In some embodiments, the primers for RT reaction preceding semi-random primed PCR-based whole transcriptome amplification include a random primer or a mixture thereof. For example, primer can be or include a random 9-mer. The RT can also include use of an oligo(dT) primer in combination with random primer. In a particular embodiment, at least one of the primers for RT is a mixture of primers that includes a random primer sequence on the 3' end of the primer, for example random 9-mer random sequence, and a common or universal primer sequence at the 5' end of the primer, which is used for binding of the universal primer of the PCR amplification step of semi-random primed PCR based methods discussed below. Accordingly, in some embodiments a random RT primer is the same as the semi-random primer discussed below. An exemplary primer is 5'-GACAT GTATCCGGATGTNNNNNNNNN-3' (SEQ ID NO:1) which includes 5' sequence including a universal primer sequence that can form a hairpin loop and includes a BciIV restriction site (underlined), and 3' random primer sequence. The RT can also include oligo(dT) primer that includes, at the 5' end, the universal primer sequence used for binding of the universal primer of the PCR amplification step of semi-random primed PCR based methods discussed below, and 3' polyT stretch. An exemplary oligo(dT) primer that can be used in combination with the exemplary random primer discussed above (SEQ ID NO:1) includes the sequence 5' GACATGTATCCGGATGTTTTTTTTTTTTTTTT-3' (SEQ ID NO:2). This primer can help ensure the recovery of the 3' end sequences of the transcripts during the second step of semi-random primed PCR amplification. Similarly as discussed above, an anchored nucleotide or nucleotides can be be added at the 3' end of the primers so as to select the mRNA over the synthetic polyA RNA carrier, i.e. to avoid the polyA RNA carrier derived, artificial cDNA. In one embodiment, it is: GACATGTATCCGGAT GTTTTTTTTTTTTTTTV-3'(SEQ ID NO: 4); and in another embodiment, it is: GACATGTATCCGGAT GTTTTTTTTTTTTTTTVN-3' (SEQ ID NO: 5).

Data indicates that when (SEQ ID NO:1) and (SEQ ID NO:2) or (SEQ ID NO: 4) or (SEQ ID NO: 5) were applied for sscDNA synthesis, followed by second-strand cDNA generation, a set of relatively short dscDNA was obtained, and fragmentation after dscDNA is not required.

C. cDNA Amplification

The methods of cDNA amplification disclosed herein are used to increase the yield of the cDNA prepared by the initial RT reaction. The cDNA amplification methods are generally based on the principles of multiple displacement amplification (MDA), or the principles of semi-random primed polymerase chain reaction. Methods based on each of the two principles can be modified to preferentially amplify total cellular RNA (referred to herein as whole transcriptome amplification) or mRNA (mRNA transcriptome amplification) based on the selection of primers used for the RT step discussed above.

1. MDA-Based Amplification cDNA-pool amplification methods based on the principles of multiple displacement amplification (MDA) are disclosed. MDA is a non-PCR based DNA amplification technique. This method can rapidly amplify small amounts of DNA to a reasonable quantity for subsequent analysis.

a. Circularization

The MDA-based cDNA amplification methods describe herein include a first step in which the cDNA prepared by an RT reaction are ligated under conditions that favor circularization. As discussed in more detail above, a 5' phosphorylated primer can be used for the RT reaction preceding MDA-based cDNA amplification. Alternatively, the cDNA can be treated to phosphorylate the 5' after the RT reaction.

The cDNA is then circularized prior cDNA amplification using a ligase. In preferred embodiments where the cDNA is double stranded, the double stranded cDNA is blunt-ended prior to or during the ligation reaction. In a specific embodiment, The END-IT™ DNA End-Repair Kit (Epicentre) plus T4 DNA ligase (Epicentre) are combined for the DNA end blunting, 5'-end phosphorylation, and ligation. This can included END-IT™ buffer 1×, 1 mM dNTPs, 1 mM ATP, 0.8 μL, total enzyme mixture, and T4 DNA ligase (0.4 U/μL). In a specific embodiment, the reaction volume is about 20 μL and carried out at room temperature for about 120 min.

Circularization and end-repair (e.g., 5' and 3' end blunting and 5' end phosphorylation) can be employed in a same tube under the same conditions.

Typical ligation is performed under conditions that drive intramolecular circularization and limits or reduces linear concatamers. These conditions lead to a more uniform amplification and more complete representation of the transcriptome compared to linear fragments. Amplification of linear fragments by MDA is more likely to amplify the middle sequences and not the end sequences, which can lead to misrepresentations during the post-amplification analysis.

The cDNA can be circularized as single stranded cDNA using, for example, CIRCLIGASE™ ssDNA Ligase. Alternatively, the cDNA can be circularized as double stranded cDNA using, for example, T4 or another double stranded ligase.

In some embodiments, the ligase preferentially catalyzes intramolecular ligation. For example, the ligase can be CIRCLIGASE™ ssDNA Ligase, which is a thermostable ATP-dependent ligase that catalyzes intramolecular ligation (i.e. circularization) of ssDNA templates having a 5'-phosphate and a 3'-hydroxyl group. CIRCLIGASE™ ssDNA Ligase ligates ends of ssDNA in the absence of a complementary sequence. The enzyme is therefore useful for making circular ssDNA molecules from linear ssDNA. Therefore in a particular embodiment, the cDNA is intramolecular circularized by CIRCLIGASE™. Experimental evidence shows that it can circularize variants of sizes of single strand cDNAs from approximately 10-bases to more than 10,000-bases of single strand cDNAs. For this circularization, the RT uses random primer (for whole transcriptome) or poly(dT) primer (for mRNA transcriptome) that are phosphorylated at their 5' end.

b. Multiple Displacement Amplification

Next, MDA can be carried out without purification or deactivation of enzyme, and without denaturation of the DNA template. The multiple displacement amplification reaction typically includes the steps of annealing primers to a DNA template, for example the cDNA, prepared by RT as described above. DNA synthesis is carried out by a high fidelity enzyme, preferentially phi29 DNA polymerase, typically at a constant temperature. Compared to conventional PCR amplification techniques, MDA generates larger sized products with a lower error frequency.

Methods of using MDA for whole genome amplification are known in the art. MDA reactions typically include diluting the DNA template in an appropriate reaction buffer ($Ca_2+$ and $Mg_2+$ free). An MDA reaction with phi29 polymerase is typically carried out at 30° C., plus or minus 1, 2, 3, 4, 5, 6, 7, 8, 9, 10, or more degrees. Preferably, the reaction is carried out a temperature between about 26° C. and 40° C. more preferably between about 28° C. and 40° C.

A typical reaction can be about 1.5-3 hours. In a particular embodiment MDA amplification of cDNA carried out with Trehalose in the reaction mixture are typically longer, for example 5, 6, 7, 8, 9, 10, 12, 13, 14, 15, 16, or more hours. Preferably the reaction is carried out for between about 10 and 16 hours. Longer reactions can increase yield.

At the end of the reaction, the enzymes are typically inactivated by heat (e.g., several minutes at about 65-75° C.) before collection of the amplified DNA products.

Some MDA methods are known in the generate template independent product (TIP). This TIP synthesis is largely oligonucleotide-derived, but exogenous DNA contamination can also contribute. When the input is limited, such as with a subnanogram amount of template DNA or a limited number of cells, TIPs are very abundant, often representing 70-75% of the total yield. TIPs can significantly impair some of the applications of the amplicon. Therefore, in some embodiments, one or more methods of reducing TIP are employed in the MDA-based cDNA amplification methods disclosed herein.

Several efforts have been made to eliminate TIP and improve the specificity of MDA (Hutchison, et al., *Nat Biotechnol.*, 24:657-658 (2006), Hutchison, et al., *Proc Natl Acad Sci USA.* 102:17332-17336 (2005), Zhang, et al, *Nature Biotechnol.*, 24:680-686 (2006), Lage, et al, *Genome Res.*, 13:294-307 (2003), Wang, et al., Nucleic Acids Res., 32:e76. (2004), Brukner, et al, *Anal Biochem.*, 39:345-347 (2005), Inoue, et al., *Nucleic Acids Res.*, 34:e69 (2006). The outstanding examples include steps for strict control of experimental procedures to avoid exogenous DNA contamination (Zhang, et al, *Nature Biotechnol.*, 24:680-686 (2006)), and minimization of the reaction volume (600 to 60 nl) (Hutchison, *Proc Natl Acad Sci USA*, 102:17332-17336 (2005), Marcy, et al. *PLoS Genet.*, 3:1702-1708 (2007)) or the reaction time (Spits C, et al., *Nat Protoc.*, 1:1965-1970 (2006)).

Preferably the disclosed MDA-based methods of cDNA amplification include one or more of the steps, reagents or principals described in Pan, et al., *Proc Natl Acad Sci USA*, 105(40):15499-15504 (2008) which is specifically incorporated by reference herein in its entirety. Pan, et al., describes an MDA approach, referred to as whole-pool amplification (WPA), which provides highly specific, unbiased, and hypersensitive amplification of very small amounts of entire genomes or complex DNA pools. In a particular embodiment, the MDA-based cDNA amplification step includes a Tre[d-(+)-trehalose dehydrate] concentration that when combined with other reaction conditions robustly or completely eliminates the production of endogenous TIP.

In a particular embodiment, the MDA-based cDNA amplification is based on the protocol discussed in the Examples below, however, it will be appreciated that the method can be modified to include alternative or additional reaction buffers or components, higher or low reaction temperatures, short or longer reaction times, modified reaction sequences, alternative reaction volumes, or combinations thereof.

In a specific embodiment described in the Examples below, circularized cDNA is combined with an amplification procedure (WPA) premixture (containing buffer, trehalose, dNTPs, primer, based on the WPA procedure described in Pan, *Proc Natl Acad Sci USA,* 105(40):15499-15504 (2008)) plus RepliPHI phi29 DNA polymerase (1,000 U/μL×0.4 μL/60 μL; Epicentre) and fresh DTT (1 mM; Invitrogen). The MDA reaction can be carried out at between about 30° C. for between about 10 and 16 hours. After the reaction, cDNA can be separated from the other reaction components. For example, cDNA can be purified using the Genomic DNA Clean and Concentrator kit (Zymo) discussed above.

MDA amplification can be carried out with, or without advanced DNA denaturation, primer annealing, and/or neutralization.

2. Semi-Random Primed PCR-Based Amplification

Semi-random primed PCR-based methods of cDNA amplification are also disclosed. A similar semi-random primed PCR amplification of Chromatin-Immunoprecipitation generated DNA was also discussed in Adli, et al., *Nat Methods*, 7(8): 615-618 (2010), which is specifically incorporated by reference herein in its entirety and including supplemental materials.

a. Reaction Procedure

Typically, cDNA amplification by semi-random primed PCR includes at least two steps. A first step includes 1, 2, 3, 4, 5, 6, or more cycles of denaturing of the cDNA, primer annealing to the cDNA, and extending of the primer. The primer utilized in the step includes a common or universal sequence, which is incorporated at the end of the cDNA and serves as a site for PCR primer binding. In some embodiments, the universal sequence was also or alternatively incorporated into the cDNA during the RT reaction. Primer extension is preferably carried out with one or more polymerases with strand displacement capability but no 3'→5' exonuclease activity. Other exemplary polymerases include, but are not limited to, exo-Bea polymerase, exo-Vent polymerase, exo-Deep Vent polymerase, exo-Bst polymerase, exo-Pfu polymerase, exo-Bca polymerase, the Klenow fragment of DNA polymerase I, T5 DNA polymerase, Phi29 DNA polymerase, phage M2 DNA polymerase, phage PhiPRD1 DNA polymerase, Sequenase, PRD1 DNA polymerase, 9° Nm™ DNA polymerase, or T4 DNA polymerase homoenzyme. In a particular embodiment, the polymerase is Sequenase V2.0 (see also See, for example, Lieb et al., *Nat. Genet.*, 28:327-343 (2001)).

Following the first step, excess semi-random primer can be inactivated, for example, by exonuclease and alkaline phosphatase treatment.

An exemplary first step protocol is described in the Example below. First, four cycles of random priming were carried out by the 3' end of a mixture of semi-random primer, a semi-random oligonucleotide with a 9-mer random nucleotide tag at the 3' end, and a universal sequence at its 5'end, which contained a hairpin structure, and a site for restriction endonuclease recognition. Using these conditions and reagents, each cDNA molecule is represented by multiple overlapping DNA constructs, each flanked by the universal sequence. The hairpin in the semi-random primer minimized the formation of primer-dimers during these steps. Excess oligonucleotide semi-random primer was digested with ExoSAP-IT.

In a particular embodiment, a first cycle include denaturing cDNA with semi-random primer and reaction buffer at about 98° C. briefly, and then annealed at about 8° C. for about 5 min. Reaction mixture including polymerase, dNTPs, DTT is added. The temperature was gradually increased to about 37° C. and incubated for about 8 min. The whole cycle can be repeated 1, 2, 3, or more time with the addition of 1.2 µl of diluted polymerase (1:4) instead of the enzyme mix.

In a second step, the product from the first step is PCR amplified using a primer that binds to the reverse complement of the universal sequence introduced at the ends of the cDNA during the first step. Reaction reagents and conditions for PCR amplification are known in the art. An exemplary PCR amplification step is described in the Examples below. Constructs can be uniformly amplified by PCR using the universal sequence of semi-random primer as the PCR primer. An exemplary PCR step can include 15 cycles of denaturation (98° C. for 30 sec), annealing (40° C. for 30 sec and 50° C. for 30 sec) and extension (72° C. for 1 min). When the Sequenase v2 is used, the lid is typically set at a low temperature, for examples at 40° C., because this enzyme is very heat-sensitive.

In a preferred embodiment, semi-random primer includes restriction sites that are incorporate into the cDNA. The restriction site are incorporated into the primer design in such a way that treat with the restriction enzyme can be used to remove most, preferable all of the universal primer sequences from the cDNA following PCR amplification. This is typically carried out by treating the cDNA with the restriction enzyme that cuts the cDNA at the introduced restriction sites. In a particular embodiment, the restriction enzyme is of Type IIs. Type IIs restriction endonucleases include, but are not limited to BmrI, HphI, MboII, and MnlI. In a specific particular embodiment, the primer 1 introduces a BciIV restriction site and the cDNA is contacted with BciIV after PCR amplification.

After the reaction, cDNA can be separated from the other reaction components. For example, cDNA can purified using the GENOMIC DNA CLEAN AND CONCENTRATOR™ kit (Zymo) or DNA CLEAN AND CONCENTRATOR™ 5 kit (Zymo) discussed above.

Reaction condition can be adjusted depending on the starting cell number of RNA quantity. For example, for 1,000-cell or 10-20 ng total RNA, PCR can include about 19-21 cycles. 2-3 more cycles can be added for every one order of magnitude fewer cells or total RNA. In the Examples below, the number of cycles was 20, 23, and 26 cycles of PCR, respectively, for total RNA equivalent to 10, 100, or 1,000 cells, respectively. This way ~500-800 ng DNA was obtained. As discussed below, in some embodiments, amplicon can be longer (100 bp to 1 kb) than the size range (100-550 bp) allowed for library construction, and fragmentation (by sonication) after removal of the artificial sequence introduced in the amplification improves the representation of the transcriptome. In a particular embodiment, a higher concentration of primers or additional more cycles of reaction in the first step shortens the size of the amplification products from the second step.

In addition to using different primers for RT, changes to the above procedure to enhance the sequence coverage, specificity, yield, reproducibility, and yield, and also to enhance differences between mRNA transcriptome verse whole transcriptome amplification can include modifications to the RNA purification steps, the reaction reagents, and reactions conditions such as those discussed in the Examples below.

In some embodiments, cDNA is collected before or after any of the above disclosed reactions using a DNA purification column, and eluted in a volume that is, or can be reduced to a small volume for the downstream reactions. Any of the purification steps can include a synthetic carrier RNA to minimize loss of cDNA.

b. Primer Design i. Semi-Random Primer

The random primer of semi-random PCR amplification, also referred to herein as semi-random primer and primer 1, is used to introduce common or universal primer sites into the cDNA. Semi-random primer is actually a mixture of primers that includes a 3' random sequence and 5' universal primer sequence. The number of primers in the mixture is determined by the number of different sequences need to randomly, but effectively, introduce the universal primer sequence onto the ends of cDNA at fragments lengths (e.g. distance between primer sites) suitable for amplification by PCR. The random sequence is a random mixture of the 4 DNA bases. The length of the random sequence in semi-random primer is typically between about 5 and 12 nucleotides, preferably, between about 6 and 11 nucleotides in length, more preferably between about 7 and 10 nucleotides in length. Random hexamer mixes consisting of 4096 sequences, are commonly used for RT reactions. The random sequence of the semi-random primer used in the Examples below is 9 nucleotides in length. Each of these primers will anneal anywhere the complementary sequence exists within a given cDNA molecule.

The universal primer sequence is of a length and sequence that is suitable for amplification of the cDNA by PCR during step 2 of the semi-random PCR amplification produced discussed above. Parameters for designing primer sequences are known in the art. For example, the universal primer sequence can be 5, 6, 7, 8, 9, 10, 11, 12, 13, 14, 15, 17, 18, 19, 20, or more nucleotides in length. Preferably, the universal primer sequence is between about 10 and about 15 nucleotides in length.

Preferably, semi-random primer includes a sequence that allows the formation of a 5' hairpin or hairpin loop to reduce or prevent primer-dimer formation. Methods of designing such a sequence are known in the art and can include, for example, a palindromic sequence. The hairpin or hairpin loop should not prevent binding and extension of the random primer sequence to the cDNA.

Preferably, semi-random primer also includes a restriction site that allows part, or preferably all, of the universal sequence to be removed from the cDNA following PCR amplification by treatment with a restriction enzyme, for example a type IIs enzyme. Suitable restriction sites are known in the art. An exemplary sequence is the restriction site for BciVI, which is GTATCC.

An exemplary primer 1 is 5'-GACATGTATCCGGAT-GTNNNNNNNNN-3' (SEQ ID NO:1), wherein "N" is (A, T, G, or C).

ii. Primer 2—Universal Primer

The sequence of a universal primer, also referred to as the common primer, or primer 2, is determined by the sequence of the 5' universal primer sequence of primer 1. The universal primer should be able to hybridize by complementary base pairing with the reverse complementary sequence generated by the universal sequence of primer 1 during the first step, and which can be extended by PCR. Therefore, the universal primer sequence typically includes a sequence that is substantially the same as the universal sequence of primer 1, or is the same as the universal sequence of primer 1.

A universal primer can that used with the exemplary primer 1 is 5'-GACATGTATCCGGATGT-3' (SEQ ID NO:3).

D. Fragmentation

MDA-based amplification procedures typically generate products of approximately 10 to 12 kb products, while semi-random primed PCR-based procedures typically generate 100 bp-1 kb products. In some embodiments, the products can be longer or shorter. For some uses of the cDNA library, for example, sequencing and microarray analysis, it can be preferred to have a cDNA library composed of cDNA having lengths predominately between about 100 and 500 base pairs. Therefore, optionally, the cDNA is fragmented. Preferably the cDNA is fragmented such that the majority of the cDNA are a size ranging from about 100 to about 550 base pairs in length. Suitable sizes can be determined based on the intended use, e.g. sequencing or microarray analysis, which are known in the art. Methods of fragmenting DNA are also known in the art and include enzymatic methods (e.g., nucleases), and mechanical methods (e.g., sonication). In a preferred embodiment, cDNA is sonicated. In another embodiment the cDNA is treated with DNase I. In some embodiments, the fragment cDNA separated by size to collect a specific size or size range of fragments for later analysis. In MDA-based methods, the library can be fragmented directly without any special treatment.

In semi-random primed PCR-based procedures, it is preferred the primer sequence is to be completely removed before fragmentation or sequencing library construction. If the typical product size resulting from semi-random primed PCR is beyond the size suitable for sequencing library construction, fragmentation can be applied before conventional sequencing library construction protocols are employed. In a particular embodiment, the amplicons from either MDA-based or semi-random primed PCR-based amplification methods are prepared for sequence directly, without fragmentation, even if the product is very long. In a preferred embodiments, the cDNA is prepared for sequencing with Nextera DNA Sample Prep Kits (ILLUMINA®).

As discussed above, for direct sequencing library construction without fragmentation on the amplicon in semi-random primed PCR, a higher concentration of primers or additional cycles of reaction in the first step can be applied to shorten the size of the amplification products from the second step.

E. Adaptors

In some embodiment, the cDNA library resulting from the amplification procedures describe herein is further modified to facilitate sequencing or microarray analysis. In a particular embodiment, the sequences are modified to include adaptors for high throughput sequencing. Exemplary adaptors that can be used are well known in the art and include, for example, ILLUMINA® adaptors. In some embodiments, particularly after fragmentation, the cDNA may require end repair and/or 3'-A addition, preferably after the ends are made blunt. Methods of repair 5' and 3' ends are known in art. For semi-random primed PCR-based methods, the removal of the amplification primer sequences by a restriction endonuclease (such as BciVI used in the Examples below) generates an overhang A at 3' end and phorphorylation 5' end, which allows a direct ILLUMINA® adapter ligation without end-repair or 3'-A addition. When the product mostly is within appropriate size, the adapter ligation can be applied directly. Adaptors are typically ligated to the ends of the cDNA and used as priming sites and barcodes for sequencing reactions. Exemplary methods of adding sequencing adaptors to the cDNA libraries prepared accordingly the methods disclosed herein are described in the Examples below.

In other embodiments, the cDNA can be spotted onto a microarray to create a library. Alternatively, cDNA can be hybridized to a known library.

The methods can be used to analyze, for example, differences in RNA expression, such as expression level, allelic expression, isoform, sequence mutation, between different cell types, or the same cell type under different conditions.

In some embodiments of the semi-random primed PCR methods disclosed herein, the universal primer sequence contains a sequence that is identical to a portion of the adapter or primers in a library for parallel massive sequencing. This sequence can be used for PCR priming for further generation of the sequencing library for parallel massive sequencing or other uses. In these embodiments, the universal sequence is not removed after the initial preparation of the cDNA library.

In some embodiments, a barcode sequence is built in during generation of the sequencing library. These embodiments can be used for parallel massive sequencing. For example, a barcoded library can be directly built for each sample, and/or multiple samples, and samples can be pooled together before second step of amplification.

III. Methods of Using cDNA Libraries

The cDNA libraries prepared according to the methods disclosed herein can be used for sequencing or microarray analysis and are typically prepared under conditions that generate cDNA representative of the mRNA or whole RNA transcript expression from the starting cell or cells. In some embodiments, the cDNA quantitatively represents of the mRNA or whole RNA transcript expression from the starting cell or cell (e.g. represents relative levels of expression between different transcripts).

The results discussed in the Examples below illustrate that the disclosed methods can be used to detect most or all of the expressed transcripts or mRNA in a single cell or low quantity of cells. The ability of the different methods disclosed herein to represent the entire transcriptome were investigated evaluating the efficiency of detection of expressed genes, and calculating reads per 1,000 bases of mRNA per million total reads (RPKM) values for annotated genes and scored the gene as present or absent based on various thresholds. The results show that the correlation of the replicates and the various levels of starting materials within each method was much closer than that observed between different methods. In each group, 100-cell and 1,000-cell samples are closely related to each other, but 10-cell samples have slightly more variability, which can of be technical variability, or the nature of the heterogeneity of different cells.

The disclosed amplification procedures produce little background DNA fragments, but these signals increase as the RNA input amount decreases, and, as such, quantitative mapping is best done by only considering reads in known CDS/UTRs under these conditions. Therefore, in some embodiments sequenced cDNA obtain according to the disclosed methods identifies 50, 60, 70, 80, 90, 95, 96, 97, 98, 99, or more percent of expressed total RNA transcripts, 50, 60, 70, 80, 90, 95, 96, 97, 98, 99, or more percent the expressed mRNA transcripts, or any combination thereof. The efficiency of detection of expressed genes can be calculated as reads per 1,000 bases of RNA per million total reads (RPKM) values for annotated genes and used to score the gene as present or absent compared to a control.

The results in the Examples below also show the methods can generate reproducible profiles. The Pearson correlation coefficient (r) can be used to measure the reproducibility. In some embodiments, the disclosed methods are able to reproduce a transcriptional profile with a Pearson correction coefficient of greater than 0.7, greater than 0.75, greater than 0.8, greater than 0.85, greater than 0.9, or greater than 0.92.

The results in the Examples below show that the disclosed methods can provide good coverage of the full length of cDNAs independent of the size. The coverage for transcripts did drop off near the very ends of transcripts (in all cases at the 5' end <10%, mostly <3-5% of the length including UTR sequence). Accordingly, in some embodiments, the disclosed methods yield a sequenced transcriptome where all represented transcripts have 5' end loss <40%, <30%, <20%, <10%, and/or 70%, 80%, 90%, 95% including UTR sequence, or more of the represented transcripts have 5' end loss <20%, <10%, <5%, or <3% of the length including UTR sequence.

In some embodiments the drop-off rate is the same or better than RNA sequencing (RNA-seq) methods without amplification, and which is also confounded by the limits of mapping of short reads to the transcripts. In some embodiments, the methods are have less 5' drop-off than other art known methods such as those discussed in Ramsköld, *Nat Biotechnol,* 30(8):777-782 (2012) which reports a drops off for ~40% of the sequences from the 5' end of 15-kb transcripts.

A cause of a loss of terminal sequences can be the shortening of the 5' end of the cDNA during second strand synthesis, or incomplete mapping. This limitation can be overcome by coupling the cDNA synthesis procedure with the incorporation of a switch mechanism at the 5' end of reverse transcript (SMART) oligonucleotide at the 5' end. For semi-random primed PCR based methods, this can be followed by adding additional SMART and poly(dT) oligonucleotides, separately incorporated with the universal sequence for capturing both 5' and 3' ends during the library generation step. Adjustment of mapping strategy for the reads can also help the recovery of the very 5 or 3' end sequences of RNAs.

Each of the disclosed methods has advantages. For example, the phi29-based method produces long products with less noise, uses an isothermal reaction and is simple to practice, very suitable for microfluidics platform. The semi-random primed PCR procedure is more sensitive and reproducible at low transcript levels or with low quantities of cells. These methods provide tools for mRNA-seq or RNA-seq when only low quantities of cells, a single cell, or even degraded RNA are available for profiling.

The methods disclosed herein can be employed in a number of way, including, for example, diagnostic assays, biomarker analysis, and screening for drug treatment mechanisms and efficacy.

IV. Kits

Kits for use with the methods disclosed herein are also disclosed. The kits for the multiple stand displacement-based methods typically include one or more reagents for lysing cells, isolating RNA from cell lysate, reverse transcription, second strand synthesis, purifying cDNA, intra-molecular oligonucleotide ligation, multiple strand displacement amplification, ligation of sequencing adaptors to oligonucleotides, or any combination thereof.

Kits for the semi-random primed PCR-based methods typically include one or more reagents for isolating RNA from cell lysate, reverse transcription, second strand synthesis, purifying cDNA, semi-random primed PCR, ligation of sequencing adaptors to oligonucleotides, restriction enzymes, or any combination thereof.

Reagents can be, for example, buffers, primers, enzymes, dNTPs, carrier RNA, and other active agents and organics that facilitate various steps of the disclosed reactions. The kits can also include instructions for use.

EXAMPLES

Example 1: Design and Development of Methods for Preparing cDNA Libraries from Very Limited Cellular Material Materials and Methods Specific experiments and the materials and methods used therein are described in the additional Examples below. A general description of the principles of the methods follows.

Methods were developed for preparing cDNA libraries for high throughput sequencing that required very limited cellular material and represented the full length of all cDNA molecules. A procedure for cDNA generation was created using a thermostable reverse transcriptase for the generation of cDNA. First strand synthesis was carried out at 50° C., below the upper temperature limit for efficient reverse transcription, in an effort to minimize effects of RNA secondary structure on the elongation of cDNA. Unless otherwise noted, the single strand cDNA (sscDNA) was converted to double-stranded form (dscDNA) by standard procedures; double strand or single strand cDNA are circularized for PMA, and double strand or single strand cDNA are applied for SMA.

Four methods for amplification of very small amounts of cDNA from LQ or single cells (FIG. 1).

Principles of a Phi29 DNA Polymerase-Based mRNA Transcriptome Amplification (Phi29-mRNA Amplification, or PMA), An exemplary PMA method is shown in FIG. 1A and includes modified elements of previous whole-genome amplification methods (Pan, et al. *Proc Natl Acad Sci USA* 105(40):15499-15504 (2008)) that depend on the high processivity and strand displacement properties of the Phi29 DNA polymerase which requires relatively long DNA templates (usually over 3-4 kb) for efficient amplification. To avoid this size dependence, the full-length cDNA were circularized using CircLigase (Epicentre) for single-stranded DNA or T4 DNA ligase for double stranded DNA prior to amplification. Small circles can be traversed more quickly by the polymerase, but this is largely compensated for by the presence of more primer binding sites on larger circles, such that the occupancy by the DNA polymerase per unit length cDNA is approximately independent of the circumference of the circle. When the DNA was sufficiently diluted such as in single cells or LQ cells, intra-molecular circles are predicted to dominate. Thus, the sequence and orientation of the cDNA fragments is representative of the original pool of molecules. A single-tube protocol without physical purification of RNA for reverse transcription and PMA, worked efficiently in cDNA generation, but the genomic DNA was less efficiently eliminated compared to the originally described protocol. Removing gDNA appears to eliminate these shortcomings.

Figure 1B:
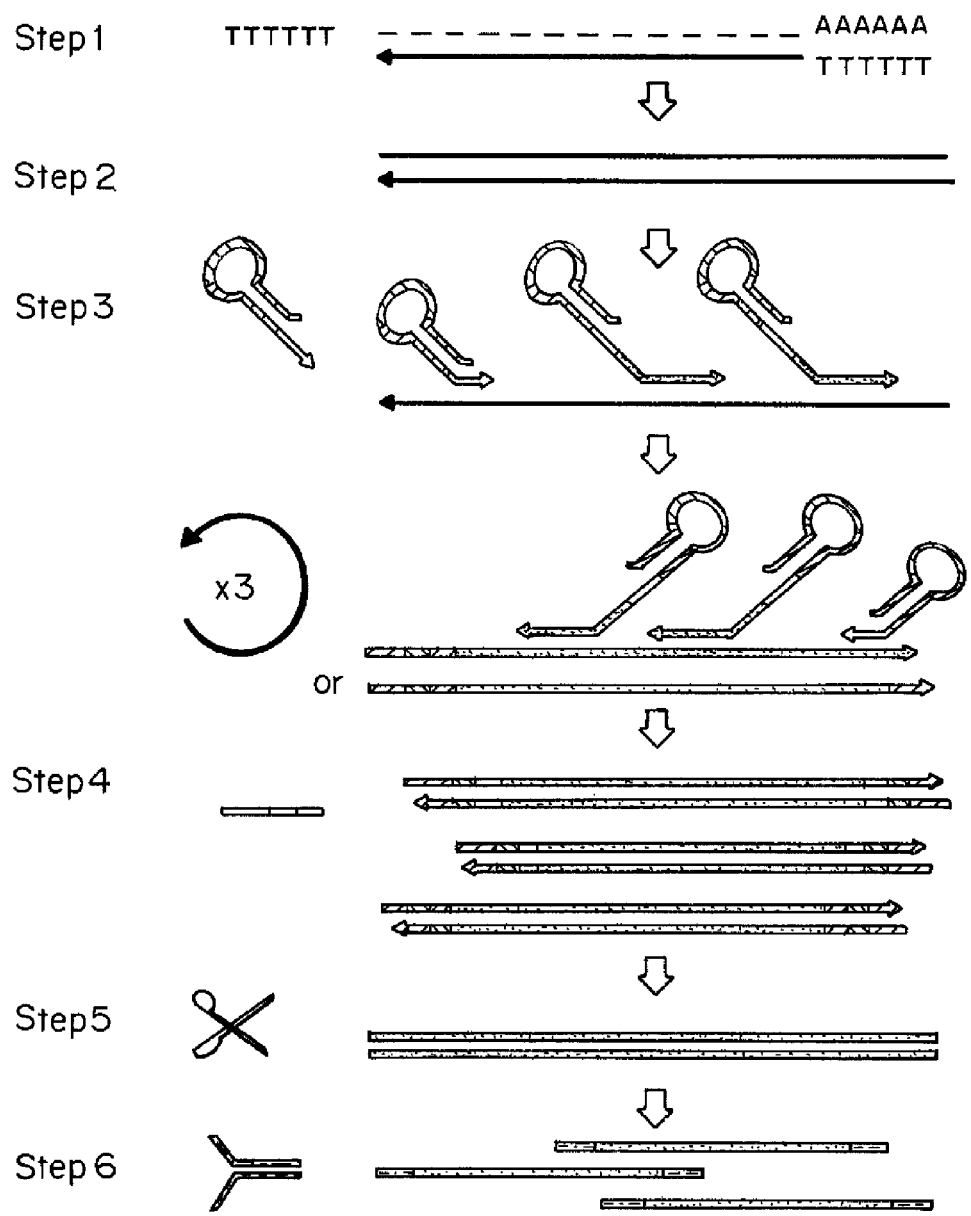
Figure 1C:
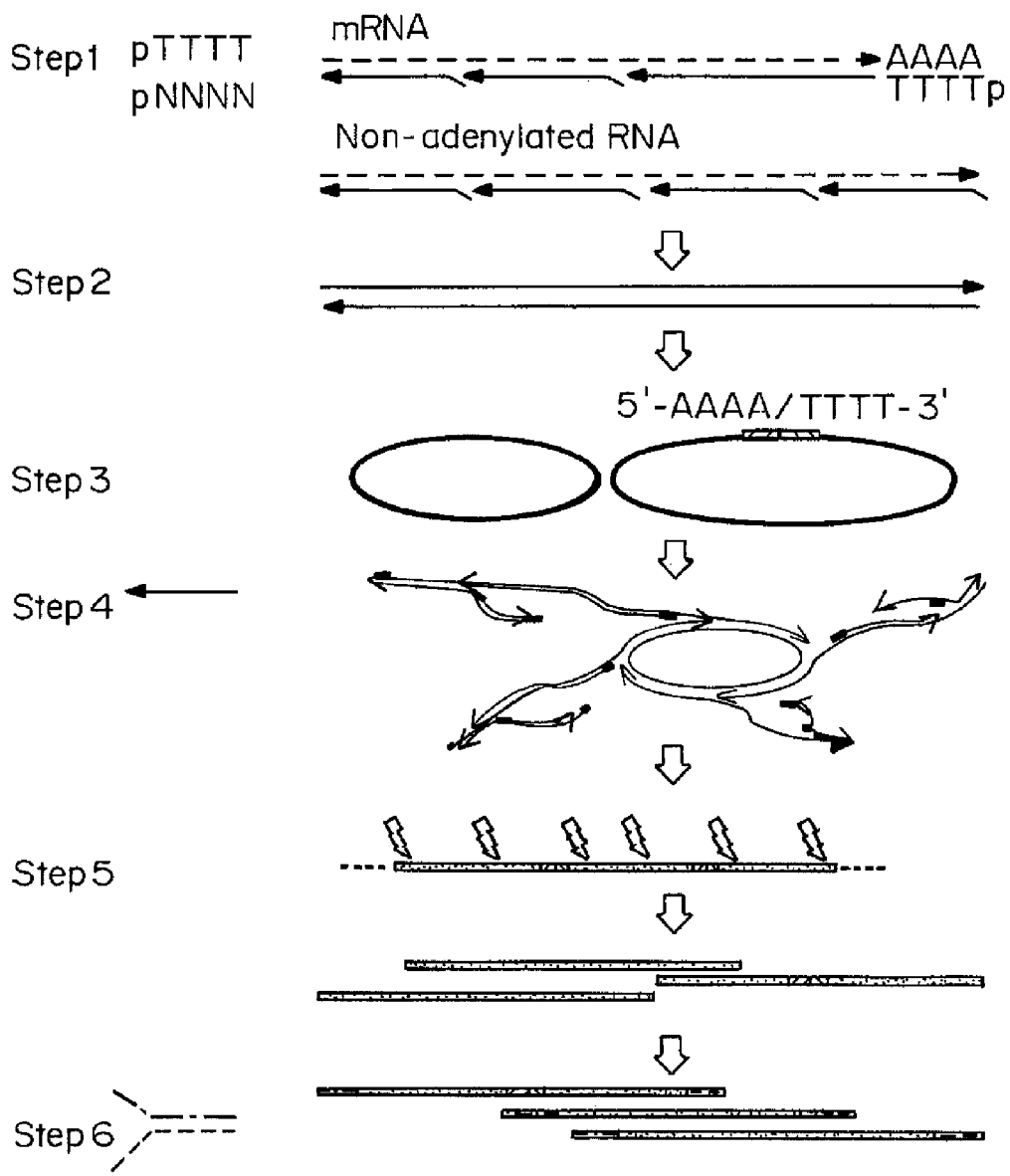

FIG. 1C shows a modified procedure, referred to as PTA, in which random primers replace oligo dT primer during the RT step.

Principles of Semi-Random Primed PCR-Based Whole Transcriptome Amplification Method (SRP-Transcriptome Amplification, or STA)

An exemplary SMA method is illustrated in (FIG. 1B). It uses oligonucleotides (SMA-p1) with random 3' sequences for capture of the whole cDNA sequence, and a universal 5' sequence that serves as a priming site for uniform PCR amplification of all cDNA fragments. The single or double stranded cDNA obtained in RT remained intact, but the method produced similar results if the cDNA was fragmented into short pieces. After the amplicon was obtained, the oligonucleotide primer was completely removed with a type IIs restriction enzyme, BciVI, whose recognition sequence was built into SMA-p1.

The method uses random priming to cover linear dscDNA or sscDNA template and potentially may not capture a short region of sequence at the extreme 5 or 3' ends of the cDNA molecules. However, in practice, this did not produce any significant sequence loss at the 3' end, especially when using anchored primers such as (SEQ ID NO: 4 and 5). Because of the semi-random-priming, each sequence can be covered by multiple different lengths of PCR templates, and because all products are of similar length and amplified with the same primer, the amplification is not subject to the well-known biases of PCR that favor shorter fragments or certain primer sequences. This enables an extensive and uniform coverage of all sequences.

Figure 1D:
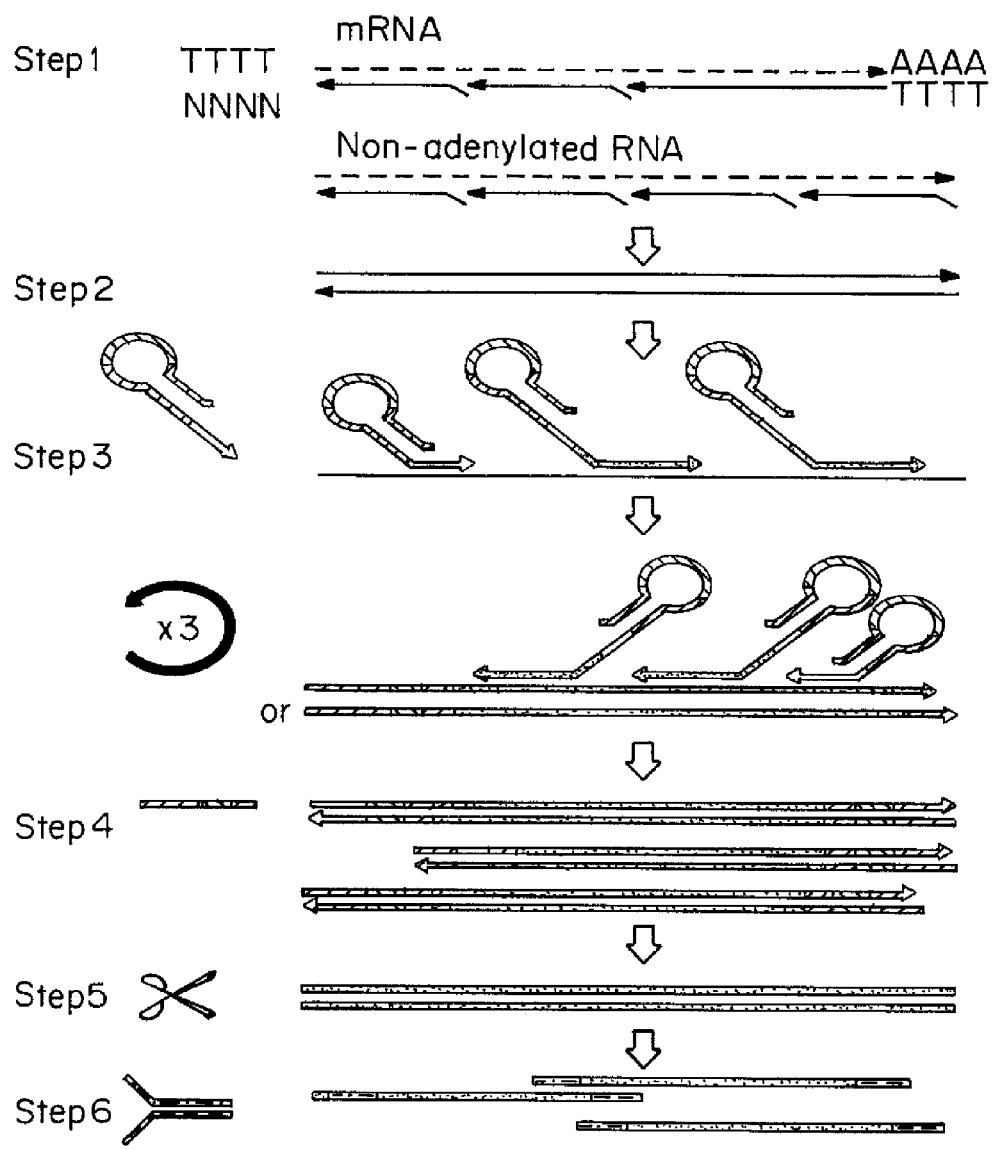
Figure 2A:
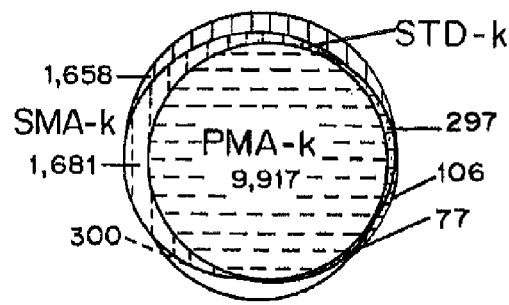
FIGS. 2A-2D are Venn diagrams illustrating the number of genes detected at >0.1 RPKM in libraries from various numbers of cells (t=10, h=100, or k=1,000) by SMA and PMA.
Figure 2B:
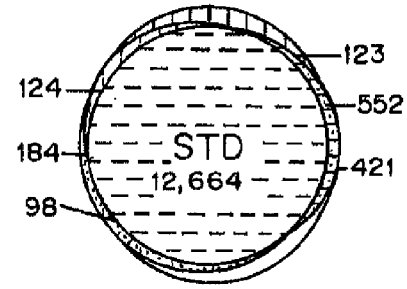
Figure 2C:
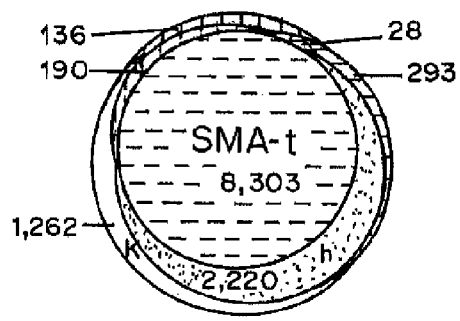
Figure 2D:
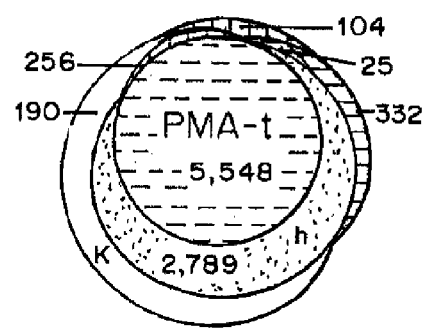

FIG. 1D shows a modified procedure, referred to as STA, in which random primers replace oligo dT primer during the RT step.

Results

Specific experiments and the results thereof are described in the additional Examples below. General conclusions gathered for development and use of the method include the following.

The PMA method did not demonstrate aberrant DNA products visualized by gel electrophoresis, unless a template was added to the reaction mixture. However, in the presence of very small amounts of template, a considerable amount of non-specific product was produced. Efficient ligation of the cDNA template was strictly required for the amplification to generate visible amounts of DNA. With the SMA method, the negative control showed some short-size primer-dimers, but these were obviously distinguishable from the amplicon derived from a template, and can be removed in the step of primer sequence removal with BciVI. The primer-dimer can easily be cut into short pieces with BciVI and removed in downstream processing. The amplicon yield with SMA, usually about 500 ng, was lower than with PMA (2-5 µg), but sufficient for quality evaluation and library construction.

The first step in the analysis of transcriptomes is typically the conversion of mRNA to cDNA. This step can be a source of substantial loss of information. The efficiency of reverse transcription and other reactions depends on an adequate and rapid mixing of liquids may be a limiting factor in some protocols (Boon, et al., *J Vis Exp.* 11(53):e3144 (2011)). Conversion from single to double stranded cDNA may also be a source of loss, particularly at the 5' end of the mRNA. This should be at least partly avoided by the use of SMART oligonucleotides that attach a known primer binding sequence to the region corresponding to the 5' end of the mRNA. However, the initial comparison of SMA with first strand cDNA and with double stranded cDNA indicates that the second strand synthesis is not a major source of signal loss.

Example 2: Comparison of PMA and SMA

Materials and Methods

Total RNA Preparation and mRNA-Selective RT

TempAssure PCR-8-tube strip, a 0.1-mL thin-well PCR tube strip with individually attached dome caps (catalog no. 1402-2900; USA Scientific) was used for all multistep reactions in this project. A protocol was adapted from the kit RNeasy Plus Micro (catalog no. 74034; Qiagen), and using the gDNA eliminator spin column before the RNeasy Minelute spin column for RNA purification. The RNA carrier provided in the kit was always added to the RLT-plus lysis buffer before homogenizing the cells. Finally, the total RNA was eluted with 14 µL 0.1×TE, and ~12 µL RNA was obtained.

For the test with various aliquots from bulk extracted total RNA, the total RNA was prepared from $5 \times 10^5$ cells using RNeasy Plus Micro kit (Qiagen) without carrier RNA. A single-tube protocol without physical purification of RNA for RT and Phi29-mRNA amplification (PMA) worked efficiently in cDNA generation, but the genomic DNA was less efficiently eliminated.

The polyadenylated RNA (mRNA) was selected from total RNA in RT using a primer 5I-phosphorylated oligo-dT24 (pdT24), with no anchoring nucleotide at the 3' end. The anchoring nucleotide reduced the RT efficiency. The 5'-phosphorylation of the oligonucleotide was optional when semirandom primed (SRP) mRNA amplification (SMA) was applied for downstream amplification. Before the first-strand cDNA (sscDNA) generation, a denaturation and primer annealing step was applied: EDTA (5 mM here, which became 3.5 mM in the 20 µL RT reaction), dNTPs (N=A, T, G, or C, each 0.5 mM in RT), and pdT24 (for PMA) or SMA-T15 (for SMA) (4 µM in RT) were added, and the tube was put in a preheated 70° C. PCR machine for 5 min and then immediately moved to an iron stand on ice.

Subsequently, the RT was carried out in a 20-4 volume, with addition of the first-strand buffer (final 1×: 50 mM Tris-HCl, pH 8.3, 75 mM KCl, and 6 mM $MgCl_2$; Invitrogen), $MgCl2$ (6 mM), DTT (2 mM; Invitrogen), RNaseOut (0.8 U/µL; Invitrogen), and SuperScript Reverse Transcriptase III (10 U/µL, SSRTIII; Invitrogen). The thermal program was set as 30° C.×5 min, 37° C.×3 min, 45° C.×3 min, 50° C.×60 min, and 70° C.×10 min, and then the sample was cooled to 4° C. When doublestrand cDNA (dscDNA) was required, the second strand was generated in a 40-µL reaction on the above product (without purification).

Additional components were added as follows: Second Strand Buffer (0.8× concentration: 16 mM Tris-HCl, 9.6 mM (NH4)2SO4, 8 mM MgCl2, 0.128 mM β-NAD; NEB), RNaseH (0.1 U/µL; Epicentre), *Escherichia coli* DNA ligase (0.125 U/µL; Epicentre), *E. coli* DNA polymerase (0.15 U/µL), and dNTPs (0.125 mM). The reaction was processed at 16° C.×120 min, followed by 70° C.×10 min for inactivation of the enzymes. The product was then purified with the Genomic DNA Clean and Concentrator kit (Zymo), where 100 ng carrier RNA (Qiagen) was added to 400 µL ChIP binding buffer before the dscDNA reaction mixture was applied. Prewarmed (60° C.) 3DEB was used for elution.

Phi29 DNA Polymerase-Based mRNA Transcriptome Amplification (PMA)

For phi29 DNA PMA, 12.5 μL elute from the dscDNA preparation above was obtained (14 μL buffer was applied for elution). The End-It DNA End-Repair Kit (Epicentre) plus T4 DNA ligase (Epicentre) were then combined for the DNA endblunting, 5'-end phosphorylation, and ligation. This included End-it buffer 1×, 1 mM dNTPs, 1 mM ATP, 0.8 μl, total enzyme mixture, and T4 DNA ligase (0.4 U/μL). The reaction volume was 20 μL and was incubated at room temperature for 120 min.

Without purification or deactivation of enzyme, and without denaturation of the DNA template, 30 μL 2× whole DNA pool amplification procedure (WPA) premixture [containing buffer, trehalose, dNTPs, random oligonucleotide N9, based on the WPA procedure (ref. 1)] plus RepliPHI phi29 DNA polymerase (1,000 U/μL×0.4 μL/60 μL; Epicentre) and fresh DTT (1 mM; Invitrogen) were added to the DNA template prepared above, with a final reaction volume of 60 μL. The reaction was carried out at 30° C. for 10-12 h and up to 16 h if more yield was desired. When the reaction was completed, 3 μL amplicon was checked on a 1-2% (wt/vol) agarose gel, and showed an ~12-kb product, whereas the blank WPA control showed no DNA.

After purification with the same Genomic DNA Clean and Concentrator kit (Zymo) column used above, 2-4 μg (or up to 8 μg when more prolonged reactions were performed) polyadenylated RNA-derived cDNA amplicon was obtained, which was then evaluated by PCR (see primers in Table 1) and fragmented for sequencing library construction.

Phi29 DNA Polymerase-Based Whole Transcriptome Amplification (PTA)

This protocol (PTA) followed the above procedure for RT and PMA, with the following exception: for the denaturation and primer annealing step before the first-strand cDNA (sscDNA) was generated, an additional random 9-mer oligonucleotide with its 5' end phosphorylated (pN9×2.0 μM, if not specified otherwise) was used in combination with the pdT24 (2.0 μM).

Semirandom Primed PCR-Based mRNA Transcriptome Amplification (SMA)

The dscDNA obtained above was amplified with a modified procedure adapted from a part of the nano-ChIP-seq protocol (Wang, et al., Nature 456(7221):470-476 (2008)). This amplification (SMA) involved three subprocedures (FIG. 1B): first, four cycles of random priming by the 3' end of SMA-p1 (5'-GACATGTATCCGGATGNNNNNNNNN-3' (SEQ ID NO:1), a semirandom oligonucleotide (with a 9-mer random nucleotide tag at the 3' end, and a universal sequence at its 5'end, which contained a hairpin structure, and a site for BciVI recognition). Each cDNA molecule was completely represented by multiple overlapping DNA constructs, each flanked by the universal sequence. The hairpin in SMA-p1 minimized the formation of primer-dimers during these steps. Second, the excess oligonucleotide SMA-p1 was digested with ExoSAP-IT (catalog no. 78200; USB), and the constructs were uniformly amplified by PCR using the universal sequence of SMA-p1 as the PCR primer, named as SMA-p2 (5'-GACATGTATCCGGATGT-3') (SEQ ID NO:3). Third, the PCR-introduced artificial sequence on the two ends of every amplicon was removed by BciVI digestion, and the amplicon derived from mRNAs was then processed to be sequencing library. The main modifications for SMA are as follows. The cDNA (dscDNA or sscDNA) was generated, purified with Genomic DNA Clean and Concentrator kit (Zymo), and eluted in 3D-EB (threefold diluted EB from Qiagen) and with a reelution using the primary elute for the best efficiency of recovery; ~10 μL elute was recovered. Higher stock concentrations of BSA (Ultrapure, 50 mg/mL, catalog no. AM2616; Ambion), dNTPs (ref no. 119969064001, when pooling 4× dNTPs, each dNTP became 25 mM; Roche), and SMA-p1 (8 μM) were used such that the volume of components added for random priming was reduced (while the final concentration remained unchanged), and the cDNA purification/elution volume above was directly applied, without concentration or volume reduction. Because of the temperature sensitivity of Sequenase, the PCR cycler lid for priming was set at 40° C. instead of 100° C. In addition, more cycles of PCR amplification with SMA-p2 at 1 μM, additional dNTPs 0.125 mM, and Phusion high-fidelity PCR master mixture with GC-rich buffer plus DMSO (NEB) were run to generate sufficient product for library construction: for 1,000-cell or 10-20 ng total RNA, this was about 19-21 cycles, and 2-3 more cycles for every one order of magnitude fewer cells or total RNA. The number of cycles was 20, 23, and 26 cycles of PCR, respectively, for the present work on SMA-k, h, and t (t, h, and k represent diluted total RNA equivalent to 10, 100, or 1,000 cells, respectively. This way, ~500-800 ng DNA was obtained. It was observed that the amplicon tended to be longer (100 bp to 1 kb) than the size range (100-550 bp) allowed for library construction, and fragmentation (by sonication) after removal of the artificial sequence introduced in the amplification improved the representation of the transcriptome.

Semirandom Primed PCR-Based Whole Transcriptome Amplification (STA)

For generation and amplification of a whole transcriptome with this method (SMA), the random oligonucleotide (SMA-p1 at 2.0 μM final concentration) was used in combination with SMAT15 (5'-GACATGTATCCGGAT-GTTTTTTTTTTTTTTT-3) (SEQ ID NO:2) (2.0 μM final) for the denaturation and primer annealing step before the first-strand cDNA (sscDNA) was synthesized. When SMA-p1 and SMA-T15 were applied for sscDNA synthesis, followed by second-strand cDNA generation, a set of relatively short dscDNA was obtained, and fragmentation after dscDNA was not required.

Library Construction and Sequencing

Standard Illumina HiSeq2000 and TruSeq protocols were principally followed for PMA/PTA library construction. The sequencing was performed on a 50-bp single end or 75-bp paired ends (PEs). For the SMA/STA amplicon when most product sizes ranged within 100-550 bp, a direct ligation to the sequencing adapter was performed after BciVI digestion. When the product was to be fragmented (for PMA/PTA products, or SMA/STA products after BciVI cutting and when a high yield and long product were obtained), the product DNA was sonicated to an ~100- to 550-bp size range on a Bioruptor Sonicator (Diagenode) with high power×5 min×5 times; the parameters were adjusted for different tests. After end-repairing, 3'-A addition, and ligation, the construct was size selected on an E-gel EX 2% (Invitrogen), and a 50-bp range of slices (300-350 bp was processed, whereas 250- to 300- and 350- to 450-bp slices were stored for back up). The DNA was purified, and one-quarter of the eluted material (5 μL) was applied for library PCR×8-10 cycles in 50 μL each (two or more PCRs might be combined) using Phusion High-fidelity DNA polymerase (NEB). For SMA or STA, when no fragmentation was applied, the BciVI-digested product was directly ligated to adapters, size selected on a gel as above, and PCR amplified for 10-12 cycles to obtain sufficient yield. The library products were size selected again on gels, and their concentration was quantitated with a Bioanalyzer (Agilent) before loading on the sequencer.

PCR Primers

Table 1 shows the PCR primer sets used for evaluation of amplicon quality. The Table includes variants of level and size of genes/transcripts (including housekeeping genes), genomic specific primers, and K562 cell-specific genes. The Titanium Taq DNA Polymerase (catalog no. 639260; Clontech) was used for PCR, usually at 25 μL, with ~5 ng (2-10 ng) of amplicon as input, running on a thermal program: 94° C.×3 min×1 cycle, followed by 94° C.×30 s, 58° C.×30 s, and 68° C.×30 s for 32 cycles (30-35 cycles), and finally 68° C.×5 min, which was then checked on a 1.5% agarose gel. TBP and GAPDH are a set of robust quality indicators for amplicons from various cell types. The primers set 4p, 5p, and 10p (Wang, et al., *Nat Rev Genet.* 10(1):57-63 (2009)) detected only a genomic-DNA specific product and was negative with qualified amplicons, whereas in parallel, gDNA or a RNA amplicon without gDNA pre-elimination showed a positive band. The long transcript (CREB1) is sensitive for evaluation of the amplicon quality for K562 in terms of the specificity and integrity. When the 5' end primers (Creb5=Creb5F+Creb5R) showed an intense PCR band, the amplicon was usually of high quality. When the middle primers (Creb=CrebF+CrebR) gave an efficient PCR amplification product, the amplicon was basically qualified. If only Creb3 (Creb3=Creb3F+Creb3R) primers resulted in a band, usually the RNA was partially degraded or the amplicon integrity was incomplete.

TABLE 1

PCR Primer Sets

| Gene ID/size/sequence ID | Primer ID | Sequences | Size, bp | Feature | SMA/PMA |
|---|---|---|---|---|---|
| CREB1, 9,794 bp (NM_134442.3) | CrebF | ACGTACAAACATACCAGATTCG | 210 | cDNA middle | High |
| | CrebR | GCACTGCCACTCTGTTTTC | | | |
| | Creb3F | TTCTACAGTATGCACAGACCAC | 147 | cDNA 3' end | |
| | Creb3R | ATGCCATAACAACTCCAGGG | | | |
| | Creb5F | TTCTCGGCTCCAGATTCCAT | 139 | cDNA 5' end | |
| | Creb5R | GGCGGAGGTGTAGTTTGACG | | | |
| TBP, 1,719 bp (NM_001172085.1) | TbpF1F | CCACCAACAATTTAGTAGTTATGAGCC | 131 | Housekeeping | High |
| | TbpR1R | CTGCTCTGACTTTAGCACCTGT | | | |
| | TbpF2F | CACCAACAATTTAGTAGTTATGAGCCA | 145 | | |
| | TbpR2R | ATGCTTCATAAATTTCTGCTCTGACTT | | | |
| GAPDH, 1,310 bp (NM_002046.3) | GapdhF | GAGTCAACGGATTTGGTCGT | 238 | Housekeeping | High |
| | GapdhR | TTGATTTTGGAGGGATCTCG | | | |
| HPRT1, 1.435 bp (NM_000194.2) | Hprt1F | TGACACTGGCAAAACAATGCA | 94 | | High |
| | Hprt1R | GGTCCTTTTCACCAGCAAGCT | | | |
| COX6A1, 593 bp (NM_004373.3) | Co6A1F | TATTCATCTTCGTAGCCAGTTGGAA | 97 | | High |
| | Co6A1R | GCATCAGGACCAAGCCGTTTC | | | |
| CDKN1A, 2,175 bp (NM_000389.4) | Cdkn1F | GCAGACCAGCATGACAGATTT | 127 | | High |
| | Cdkn1R | ATGTAGAGCGGGCCTTTGAG | | | |
| KRP1, 14,905 bp (NM_002332.2) | Lrp2F | GTCCCAGCCACGGTGATAG | 126 | cDNA middle | Not in K562 |
| | Lrp2R | CGCATCTTCTTCAGCGACAT | | | |
| | Lrp23F | GTCACCCACCTCAACATTTCA | 129 | cDNA 3' end | Not in K564 |
| | Lrp23R | GTTCTCGCCCTTCATCTGC | | | |
| | Lrp25F | ATTGAAGTGGTGGACTATGAGGG | 123 | cDNA 5' end | Not in K566 |
| | Lrp2R | GGCATTGTCCGAGTTGGTG | | | |
| 4p (chromosome 4p) | 4pF | AACTGAATGGCAGTGAAAACA | 150 | gDNA only | Not in cDNA |
| | 4pR | CCCTAGCCTGTCATTGCTG | | | |
| 5p (chromosome 5p) | 5pF | GGGTAAGATCCAGAGCCACA | 224 | gDNA only | Not in cDNA |
| | 5pR | CTCATTCCTTCTCGAAGCA | | | |
| 10p (chromosome 10p) | 10pF | GTTCTGCTGCCTCTACACAGG | 207 | gDNA only | Not in cDNA |
| | 10pR | ATCCTTCTGTGAACTCTCAAATC. | | | |
| HBA1, 576 bp (NM_000558.3) | Hba1F | CGGAGGCCCTGGAGAGGATGT | 211 | K562 specific | High |
| | Hba1R | ACCGGGTCCACCGAAGCTT | | | |
| LMO2, 2,303 bp (NM_005574.3) | Lmo2F | ATCTCAGGCTTTTTGGGCAAGACG | 201 | K562 specific | High |
| | Lmo2R | ACTCGTAGATGTCCTGTTCGCACA | | | |
| GATA1, 1,501 bp (NM_002049.3) | GataF | CCTCCCTGTGAGGCCAGGGA | 153 | K562 specific | High |
| | GataR | GCGCTTCTTGGGCCGGATGA | | | |
| HBG1, 584 bp (NM_000559.2) | HbgF | ACCCTGGGAAGGCTCCTGGT | 187 | K562 specific | High |
| | HbgR | TCAGCTGGGCAAAGGTGCCC | | | |

Results

To compare the two methods, a batch of K562 erythroleukemic cell RNA was made from 5×10$^5$ cells, and diluted aliquots equivalent to 1000 (k), 100 (h), and 10 (t) cells of RNA. cDNA was prepared from duplicate aliquots of each RNA concentration by either PMA or SMA and the resulting amplified products sequenced to a depth of at least ten million total reads for each sample.

Mapping distribution for cDNA sequence reads from coding sequences (cds), seeded synthetic oligonucleotides (ercc), intergenic sequences (intergenic), introns (intron), mitochondria (mitochond), sequences overlapping more than one type of target (overlap), ribosomal RNA sequences (ribosomal), and 3' and 5' untranslated regions (utr) of mRNA were obtained by SMA and PMA amplicons for different numbers cells and different concentrations of primers, and for unamplified controls (STD). The results were compared, and indicate that both PMA and SMA, the mappable reads and the fractions of sequencing reads that mapped to the coding regions, the 3' and 5' UTRs, ribosomal RNA and intergenic genomic DNA, were roughly similar (Table 2 and Table 3).

TABLE 2

Distribution of Sequencing Reads: Mappable Read Number and Mappable Ratio

| Sample ID | Total read (no.) | Map read (no.) | Map ratio (%) |
|---|---|---|---|
| STD1 | 5.59E+07 | 3.51E+07 | 62.80 |
| STD2 | 1.69E+08 | 1.32E+08 | 78.36 |
| STD3 | 1.99E+08 | 1.36E+08 | 68.17 |
| SMA-t1 | 5.77E+07 | 2.84E+07 | 49.20 |
| SMA-t2 | 5.53E+07 | 3.23E+07 | 58.37 |
| SMA-h1 | 6.39E+07 | 3.86E+07 | 60.30 |
| SMA-h2 | 5.64E+07 | 3.92E+07 | 69.44 |
| SMA-k1 | 5.71E+07 | 3.69E+07 | 64.61 |
| SMA-k2 | 5.50E+07 | 3.73E+07 | 67.88 |
| PMA-t1 | 4.01E+07 | 2.07E+07 | 51.73 |
| PMA-t2 | 3.68E+07 | 2.86E+07 | 77.72 |
| PMA-h1 | 5.50E+07 | 4.41E+07 | 80.13 |
| PMA-h2 | 4.39E+07 | 3.37E+07 | 76.61 |
| PMA-k1 | 5.40E+07 | 4.53E+07 | 83.87 |
| PMA-k2 | 4.20E+07 | 3.10E+07 | 73.89 |
| PMA-c5t | 2.40E+07 | 1.48E+07 | 61.86 |
| PMA-c1h | 3.00E+07 | 1.22E+07 | 40.88 |
| PMA-c1k | 2.18E+07 | 1.33E+07 | 60.96 |
| PTA1-1 | 2.60E+07 | 1.37E+07 | 52.59 |
| PTA1-2 | 3.03E+07 | 1.64E+07 | 54.24 |
| PTA2-1 | 1.05E+07 | 3.70E+06 | 35.23 |
| PTA2-2 | 1.77E+07 | 6.43E+06 | 36.37 |
| PMA-cs | 3.64E+07 | 9.92E+06 | 27.27 |

TABLE 3

Distribution of Sequencing Reads: Read Distribution

| Sample ID | CDS + UTR (no.) | CDS + UTR (%) | CDS (%) | 5'UTR (%) | 3'UTR (%) | Ribosomal (%) | Mitochondrial (%) | Junction (%) | Intergen (%) | Intron (%) | Overlap (%) | Adapter (%) |
|---|---|---|---|---|---|---|---|---|---|---|---|---|
| STD1 | 2.42E+07 | 69.00 | 47.84 | 2.90 | 18.26 | 4.03 | 6.59 | 0.29 | 0.99 | 11.14 | 7.95 | 0.00 |
| STD2 | 8.74E+07 | 66.01 | 43.70 | 3.14 | 19.18 | 2.07 | 9.12 | 0.30 | 1.27 | 13.64 | 7.59 | 0.00 |
| STD3 | 8.94E+07 | 65.89 | 47.95 | 3.07 | 14.87 | 6.79 | 8.34 | 0.78 | 1.38 | 8.55 | 8.27 | 0.00 |
| SMA-t1 | 1.53E+07 | 53.77 | 36.29 | 1.42 | 16.06 | 1.56 | 11.62 | 0.21 | 0.43 | 9.56 | 7.16 | 15.68 |
| SMA-t2 | 1.25E+07 | 38.63 | 27.66 | 0.99 | 9.97 | 4.30 | 7.10 | 0.22 | 0.53 | 11.93 | 4.79 | 32.51 |
| SMA-h1 | 2.02E+07 | 52.33 | 36.31 | 1.45 | 14.57 | 1.88 | 11.08 | 0.31 | 0.94 | 10.11 | 6.82 | 16.52 |
| SMA-h2 | 1.64E+07 | 41.76 | 29.83 | 1.10 | 10.83 | 5.96 | 7.53 | 0.33 | 1.03 | 12.30 | 5.35 | 25.74 |
| SMA-k1 | 1.80E+07 | 48.82 | 34.45 | 1.56 | 12.81 | 3.61 | 11.88 | 0.40 | 1.48 | 9.45 | 6.32 | 18.03 |
| SMA-k2 | 1.51E+07 | 40.41 | 30.40 | 1.17 | 8.84 | 14.60 | 7.99 | 0.43 | 1.40 | 12.53 | 5.19 | 17.44 |
| PMA-t1 | 1.76E+07 | 84.98 | 61.49 | 0.81 | 22.69 | 0.14 | 0.00 | 0.21 | 0.10 | 9.08 | 5.46 | 0.02 |
| PMA-t2 | 2.14E+07 | 74.99 | 54.57 | 1.28 | 19.13 | 7.47 | 0.00 | 0.25 | 0.26 | 9.62 | 7.38 | 0.02 |
| PMA-h1 | 3.69E+07 | 83.64 | 62.38 | 1.54 | 19.73 | 0.63 | 0.00 | 0.28 | 0.37 | 9.05 | 5.96 | 0.06 |
| PMA-h2 | 2.50E+07 | 74.18 | 53.37 | 1.48 | 19.33 | 8.83 | 0.02 | 0.35 | 0.51 | 10.65 | 5.41 | 0.04 |
| PMA-k1 | 3.79E+07 | 83.66 | 61.67 | 1.43 | 20.56 | 0.62 | 0.00 | 0.36 | 0.55 | 8.09 | 6.71 | 0.01 |
| PMA-k2 | 2.14E+07 | 68.81 | 50.09 | 1.09 | 17.63 | 9.57 | 0.02 | 0.49 | 1.19 | 13.92 | 5.98 | 0.02 |
| PMA-c5t | 9.45E+06 | 63.64 | 40.90 | 0.97 | 21.77 | 15.26 | 0.08 | 0.76 | 0.30 | 8.75 | 11.16 | 0.06 |
| PMA-c1h | 7.91E+06 | 64.55 | 40.52 | 1.21 | 22.83 | 13.39 | 0.81 | 0.86 | 0.35 | 9.53 | 10.48 | 0.02 |
| PMA-c1k | 1.01E+07 | 76.02 | 40.36 | 1.02 | 34.64 | 2.79 | 0.04 | 1.04 | 0.44 | 10.18 | 9.47 | 0.01 |
| PTA1-1 | 5.06E+06 | 36.97 | 21.40 | 0.74 | 14.84 | 31.24 | 0.54 | 1.85 | 2.58 | 17.38 | 5.59 | 0.00 |
| PTA1-2 | 6.46E+06 | 39.30 | 23.42 | 0.74 | 15.13 | 30.95 | 0.53 | 1.77 | 2.56 | 15.94 | 5.46 | 0.01 |
| PTA2-1 | 4.90E+05 | 13.26 | 8.22 | 0.53 | 4.51 | 62.75 | 3.14 | 1.28 | 1.74 | 12.09 | 2.93 | 0.01 |
| PTA2-2 | 7.85E+05 | 12.20 | 7.53 | 0.50 | 4.18 | 64.96 | 3.03 | 1.19 | 1.61 | 11.54 | 2.75 | 0.01 |
| PMA-cs | 2.02E+06 | 20.38 | 12.12 | 0.82 | 7.43 | 56.03 | 0.06 | 0.20 | 0.64 | 20.42 | 2.26 | 0.00 |

For Tables 2-6, t, h, and k represent diluted total RNA equivalent to 10, 100, or 1,000 cells, respectively. PMA-ct5, PMA-c1h, PMA-c1k corresponds to cDNA prepared from cell lysates (cs: single cell; c5t: 50 cells; ch: 100 cells; ck: 1,000 cells). PTA refers to the libraries obtained by random plus oligo-dT priming of RT beginning with total RNA equivalent to 3,000 (3 k) cells of an acute promyelocytic leukemia cell line, NB4. PTA-a (PTA-1, 2) used less random primers than in PTA-b (PTA-3, 4). K562 control (i.e., STD) was from RNA-seq with conventional protocol and represents three biologic replicates of K562 cell RNA prepared from a large culture (each >2 million cells), converted to cDNA, and sequenced without a preliminary amplification.

The percentages for CDS, UTR, and other components are their reads against the total mappable reads. STD1, 2, and 3 each was sequenced with a whole lane. The libraries for PTA, PMA-c5t, -ch, and -ck were generated with amplicons and each was multiplex sequenced (1×50) in a one-eighth lane. PMA-cs was sequenced (2×75) at one-half lane. All other six PMA and six SMA libraries and multiplex sequenced (1×50) at one-sixth lane.

SMA reads contain significant reads for adapter sequences due to an occasional technical imperfection. SMA contains significant mitochondrial sequences. PTA samples and PMAcs show abundant ribosomal reads. All samples including STDs detect ~10% or more intron sequencing probably from prematured RNA, with very little intergenic sequences, indicating little genomic DNA contamination.

Sequencing features for PMA and SMA amplicons vs. standard controls (STD) were also analyzed. The GC content distribution of products were determined by dividing the transcripts into 100 equal segments (100 bins, 5' to 3' end from bottom to top). The average GC content profile in the transcripts was also similar, although in SMA it was slightly reduced. The CG content of the single cell (PMA-cs) transcriptome showed a little disturbed pattern, probably due to lower read number, more rRNAs, and/or other causes, but overall it is similar to other amplicons.

In addition, a significant number of reads of intron sequences was detected, 10 to 20-fold more than the number of reads of intergenic sequences (Tables 2 and 3). This indicates that the intron sequences were derived from immature mRNA, rather than gDNA contamination.

The percent of mappable reads were also analyzed for SMA, PMA, and compared to native controls. The majority of fragments were sequenced only once and the number of fragments sequenced twice or more was less than one third of the total, indicating that substantially fewer than one third of the fragments in the cDNA mixture had been identified, even with preparations from as few as ten cells. In addition, the mappable read number was lower in amplicons from smaller numbers of cells: 10-cells <100-cells ~1000-cells <STDs (standard controls) (Tables 2 and 3), indicating that less cell input generated relatively more un-mappable noise. Overall, the percentage of unique reads for SMA was comparable to STD, but for PMA with diluted RNA it was a little higher, and for PMA directly with low number of cells it was lower. PMA also showed more cDNA copies of ribosomal RNA when a sample with fewer cells was directly amplified.

When PTA was performed, the amplicons contained reduced rRNA representation compared to the original rRNA content of the preparation, and sequences of annotated RNA other than rRNA sequences, represented up to approximately 25% of the total reads. This makes it possible to apply PTA for partially degraded RNA samples and for the case when a whole transcriptome rather than just mRNA is desired. SMA was also performed after only first strand cDNA synthesis and obtained results that were close to those from double stranded cDNA. Initial experiments with single strand circle formation and PMA succeeded for low numbers of cells and single cells. Later batches of the CircLigase enzyme (Epicentre) used for the ligation did not work well for larger circles. However, it is apparent from the PTA data discussed below that phosphorylated random primers would generate small single-stranded-circles that could be ligated efficiently and used for single cell profiling.

STA amplicons were also prepared from approximately 100-cells equivalent RNA. PCR evaluation included STA with different concentrations of random primer SMA-p1 in combination with SMA-T15. 100-cell equivalent of RNA of K562 was demonstrated. Concentrations in RT: SMA-T15, 4 μM; SAMp1 in STA1, 6.7 μM; SMA-p1 in STA2, 0.3 μM. The random primer concentration SMA-p1 can be used in a wide range of concentrations. The PCR evaluation results indicated a satisfactory detection of transcripts.

Overall, the results show that in comparison with PMA, SMA detects more genes, gives a pattern closer to that obtained from RNA-seq of unamplified cDNA, and is more sensitive with small amounts of starting material. In addition, SMA is probably more suitable for single cell RNA amplification on the bench top. When combined with magnetic capturing mRNA directly from cell lyste, followed by a direct reverse transcription, a high throughput process of expression profiling should be practical. A similar semi-random PCR strategy of SMA is used in a commercial kit (Transplex Whole Transcriptome Amplification or WTA, from Sigma-Aldrich). WTA performs well in microarray analysis, compared to some other methods (Gonzalez, et al., *PLoS ONE*. 5(12):e14418 (2010)), but uses long artificial primer sequences not designed to be removed after amplification. Thus its use has not been reported in conjunction with high throughput sequencing.

With PMA, incomplete representation of low abundance mRNAs was observed when LQ cells were processed, with sequences missing from the 3' end of the original mRNA. This indicates that the loss of these sequences occurs before or during cDNA circularization, perhaps due to exonuclease action during blunt end generation and ligation, or to incomplete ligation of segments of DNA from the second strand to give the full-length product. However, the sequence loss was at least partly random as it was not consistent from sample to sample of the same cell type. Although PMA is somewhat less sensitive than SMA, PMA has certain advantages. In principle, it generates intact full-length copies of cDNAs that would be suitable for longer sequence runs as technology becomes available. These full-length cDNAs would be important for resolution of ambiguities in assigning splice isoforms (Au, et al., *PLoS ONE*. 7(10):e46679 (2012)).

PMA has a particular advantage for application to closed microfluidic systems. This would allow a large number of single cells to be amplified in parallel. It is relatively simple in operation as the steps of manipulations and the number and range of changes of temperature are very limited. Alternatively SMA could be performed in microfluidic apparatus that have PCR capability (Fluidigm). Carrying out reactions in nanoliter volumes has the potential to substantially improve single cell work (Boon, et al., *J Vis Exp*. 11(53):e3144 (2011), Lecault, et al., *Curr Opin Chem Biol* 16(3-4):381-390 (2012), Boon, et al., *Biotechniques*. 50(2): 116-119 (2011), Marcus, et al., *Anal Chem*. 78(9):3084-3089 (2006), Zhong, et al., *Lab Chip*. 8(1):68-74 (2008)). The literature reports that the conversion of small amounts of mRNA to cDNA is more efficient in very small volumes, and may reach 50% compared to conventional methods that yield as little as 10% (Zhong, et al., *Lab Chip*. 8(1):68-74 (2008)). Also, the use of small volumes makes it possible to carry out reactions with amounts of enzyme that are more proportionate to the amount of nucleic acid present. However, because the initial amplification is limited, when working in small volumes, a second stage amplification may be needed to obtain enough material for some analyses.

Example 3: All Lengths of Transcripts were Covered Over their Full Lengths

Materials and Methods
Alignment
RNA sequencing (RNA-seq) reads were aligned to the HG19 genome using TopHat (v2.02). Base-level quantitation of genes and genic features were derived using BEDTools and the RefSeq reference transcriptome, as well as the R-make RNA-Seq analysis package (http://physiology.med.comell.edu/faculty/mason/lab/r-make/).
Results
After sequencing, reads were mapped to the human genome (hg19) using TopHat (Trapnell, et al., *Nat Protoc*.

7(3):562-578 (2012)). The result demonstrated that, in general, all lengths of transcripts were covered over their full lengths. Some of the results are shown in Tables 4-6.

TABLE 4

Reproducibility of PMA

| Sample ID | PMA-t1 | PMA-t2 | PMA-h1 | PMA-h2 | PMA-k1 | PMA-k2 |
|---|---|---|---|---|---|---|
| PMA-t1 | 1.000 | 0.715 | 0.344 | 0.579 | 0.594 | 0.511 |
| PMA-t2 | 0.715 | 1.000 | 0.561 | 0.315 | 0.719 | 0.704 |
| PMA-h1 | 0.344 | 0.561 | 1.000 | 0.713 | 0.854 | 0.813 |
| PMA-h2 | 0.679 | 0.816 | 0.713 | 1.000 | 0.856 | 0.847 |
| PMA-k1 | 0.594 | 0.719 | 0.854 | 0.856 | 1.000 | 0.927 |
| PMA-k2 | 0.511 | 0.704 | 0.813 | 0.847 | 0.927 | 1.000 |

The comparison in Table 4 was performed using the Pearson correlation coefficient method (showing value r, see SI Materials and Methods for details) with sequencing reads of CDS and 5' and 3' UTRs (>0.1 RPKM) detected in replicate amplifications from 10 (t), 100 (h), or 1,000 (k) cells.

TABLE 5

Reproducibility of SMA

| Sample ID | SMA-t1 | SMA-t2 | SMA-h1 | SMA-h2 | SMA-k1 | SMA-k2 |
|---|---|---|---|---|---|---|
| SMA-t1 | 1.000 | 0.965 | 0.983 | 0.939 | 0.955 | 0.900 |
| SMA-t2 | 0.955 | 1.000 | 0.978 | 0.979 | 0.944 | 0.924 |
| SMA-h1 | 0.983 | 0.978 | 1.000 | 0.961 | 0.974 | 0.930 |
| SMA-h2 | 0.939 | 0.979 | 0.961 | 1.000 | 0.938 | 0.957 |
| SMA-k1 | 0.956 | 0.944 | 0.974 | 0.938 | 1.000 | 0.963 |
| SMA-k2 | 0.900 | 0.924 | 0.930 | 0.957 | 0.963 | 1.000 |

The comparison in Table 5 was performed using the Pearson correlation coefficient method (showing value r, see SI Materials and Methods for details) with sequencing reads of CDS and 5' and 3' UTRs (>0.1 RPKM) detected in replicate amplifications from 10 (t), 100 (h), or 1,000 (k) cells.

TABLE 6

Reproducibility of STD

| Sample ID | STD1 | STD2 | STD3 |
|---|---|---|---|
| STD1 | 1.000 | 0.968 | 0.972 |
| STD2 | 0.968 | 1.000 | 0.948 |
| STD3 | 0.972 | 0.948 | 1.000 |

The comparison in Table 6 was performed using the Pearson correlation coefficient method (showing value r) with sequencing reads of CDS and 5' and 3' UTRs (>0.1 RPKM) detected in replicate samples.

To display the general coverage of cDNAs, each annotated cDNA (including CDS and 5' and 3' UTR) was divided into one hundred parts. The relative intensity along each one-hundredth for all cDNAs was summed and plotted. The results indicate that both methods were able to represent almost the entire length of the cDNA.

To further evaluate the effect of cDNA length on coverage, the cDNAs were divided into five length categories according to their length and plotted the intensity of representation for each one hundredth of the cDNAs in each length category. The results show that there was good coverage of the full-length of cDNAs independent of the size. Although the coverage for transcripts did drop off near the very ends of transcripts (in all cases at the 5' end <10%, mostly <3-5% of the length including UTR sequence), this range of drop-off is not significantly worse than all current sequencing RNA-seq methods without amplification, and is confounded by the limits of mapping of short reads to the transcripts, as well as other causes. In this aspect PMA and SMA are superior to a recently reported method, which drops off approximately 40% of the length at the 5' end for 15 kb transcripts (Ramsköld, et al., Nat Biotechnol. 30(8): 777-782 (2012)).

For the PMA protocol, one cause for this drop-off is the failure to map the reads derived from the poly-A tail and 5' end chimerical sequences joined during circularization. This can be improved through advances in the bioinformatic analysis or genome indexing. Another cause of a loss of terminal sequences may be the shortening of the 5' end of the cDNA during second strand synthesis. This could also be potentially overcome by coupling the cDNA synthesis procedure with the incorporation of a SMART oligonucleotide at the 5' end (Zhu, et al., Biotechniques 30(4):892-897 (2001)). For SMA, this may be followed by adding additional SMART and poly-dT oligonucleotides separately incorporated with the universal sequence for capturing both 5' and 3' ends during the library generation step (step 3, FIG. 1A).

In summary, each of the two procedures demonstrated full-length coverage of the RNA sequences, independent of the length of the transcripts, with cDNA as long as 23 kb. These procedures also covered the 3'UTRs and 5'UTRs.

Example 4: Expressed Genes are Efficiently Detected, and Results are Reproducible Materials and Methods
  Gene Counts
  Total gene alignment counts from exons and UTRs were normalized to reads per thousand bases of mRNA per million total reads (RPKM) values that were used for further analysis. The overlap between samples and preparations were identified by minimum RPKM values. Except when otherwise stated, average values between samples of identical cell number input and preparations were calculated, and common minimum detection levels were used to gauge similarity between the preparation methods and cell number inputs. The correlation between samples was derived from normalized RPKM values of coding sequence (CDS) and 5' and 3' UTRs using the Pearson correlation coefficient.
Results
  To evaluate the efficiency of detection of expressed genes, RPKM values were calculated for annotated genes, and scored the gene as present or absent based on various thresholds. Venn diagrams illustrating the number of genes detected at >0.1 RPKM in libraries from various numbers of cells (t, h, or k) with two methods: SMA and PMA are shown in FIGS. 2A-2D. The gene number for each level is an average of two replicates. RNA-seq reads were assembled by Cufflinks with the RefSeq GTF file as a reference annotation. Numbers represent the numbers of genes detected in various overlapping subsets. The Venn Diagrams in FIGS. 2A-2D show the decline in the numbers of genes detected as the amount of input RNA declined, and also the relative coverage by extensive sequencing of unamplified cDNA compared with the coverage by PMA and SMA.

Both amplification procedures produce background DNA fragments. These signals increase as the RNA input amount decreases, and, as such, quantitative mapping is best done by only considering reads in known CDS/UTRs. SMA produces relative more spurious fragments that match genomic DNA at apparently random regions. One possibility for the cause of these spurious fragments is that more of these sequences appear as a result of the amplification of very short sequences of incompletely digested genomic DNA although these also occur in standard RNA-seq (Table 2).

Other un-mappable reads contribute to the relatively lower mapping rate for LQ cells, especially single cells. This includes any possible contamination of trace amounts of DNA from lab environment or reagents, or some artificial DNA generated by the method, as has also been observed in other reports of RNA amplification methods. The consequence of these noise DNA fragments is that a progressively smaller number of reads map to cDNA sequences as the input template is decreased and more sequencing runs are needed to obtain the desired coverage of cDNA sequences.

To compare the reproducibility and accuracy of both methods, counts per Kb of CDS/UTRs were determined in the various amplified samples and STD (see Table 2 for the read number). Heatmaps comparing gene detection with libraries amplified with PMA and SMA were prepared comparing replicates with each analysis at different levels of RNA inputs versus STD. The analysis was on the basis of the genes that were detected at >0.1 RPKM, regardless of the intensity of their signals.

The results indicate that within each method, amplicons were overall better correlated than were amplicons prepared from the same level of samples with the two different methods. Input RNA from as low as 10-cells in each method missed some of the weakly expressed cDNAs, but the cDNAs missed by the two methods were often divergent. More abundant cDNAs were generally well represented when either method was used for cDNA amplification. This is similar to results shown in (Ramsköld, et al., *Nat Biotechnol.* 30(8):777-782 (2012)). The general pattern of SMA is closer than PMA to STD. SMA also has better reproducibility.

Several samples were correlated on the basis of the relative levels of RPKM for each gene. Heatmaps were prepared for sequencing results with PMA and SMA amplicons (and reference STD) for comparison of RPKM profiles of genes detected (threshold: RPKM >0.1) in replicate experiments with amplified cDNA corresponding to t, h, or k cells, with 12,640 genes covered. The results indicate that the correlation of the replicates and the various levels of starting materials within each method were much closer than that observed between different methods. In each group, 100-cell and 1000-cell samples are closely related to each other, but 10-cell samples have slightly more variability, especially for PMA. Each method (SMA, PMA) produces reproducible profiles (Table 3). The Pearson correlation coefficient (r) was consistently >0.9 for SMA samples even when 10-cell RNA was amplified. When a 1000-cell sample was amplified, the r (0.96) was comparable to the technical repeats of the standard RNA-seq without amplification. For PMA, the r was >0.925 for two 1000-cell samples, and 0.715 for the two 10-cell samples tested.

In summary, the reproducibility is higher within each method than between the 2 methods, and, for PMA, also higher when more cells are used. When more starting material was used, the number of genes detected was increased. Because different procedures show somewhat different transcript patterns, for any given biological test, it is necessary to use a consistent procedure throughout the analyses.

Example 5: PMA and SMA can be Use for Single Cell Transcriptome Sequencing

Materials and Methods

Single K562 erythroleukemic cells were manually isolated from suspension culture and subjected to PMA-based RNA isolation, cDNA amplification, and sequencing.

The same analyses was applied to a set of single murine dorsal root ganglion cell bodies, each individually harvested by suction applied by a micropipette from an intact ganglion whose cells were loosened from their cellular neighbors by prior topical application of collagenase.

Results

Figure 3A:
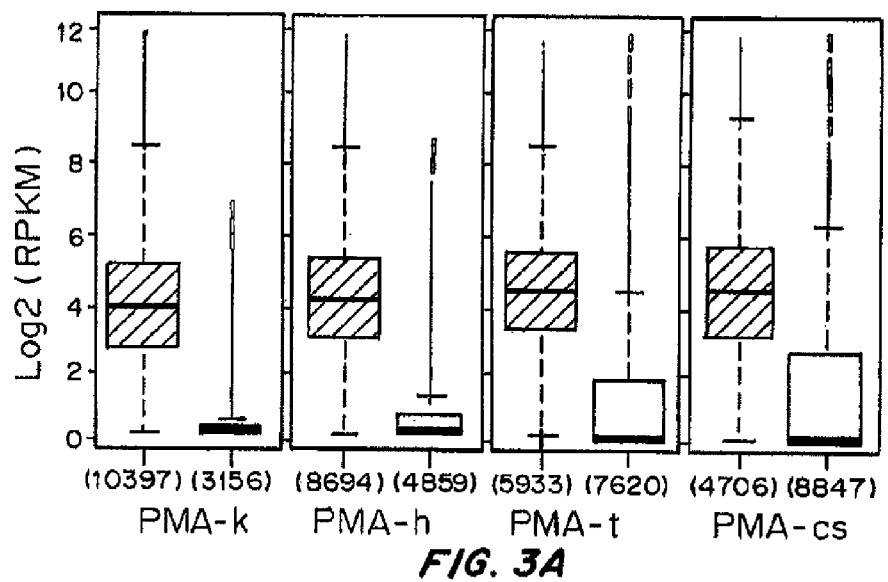
FIGS. 3A-3B are box plots showing the $\log_2$(RPKM) gene numbers detected (RPKM>0.1) or missed (RPKM≤0.1) by PMA (FIG. 3A) and SMA (FIG. 3B).
Figure 3B:
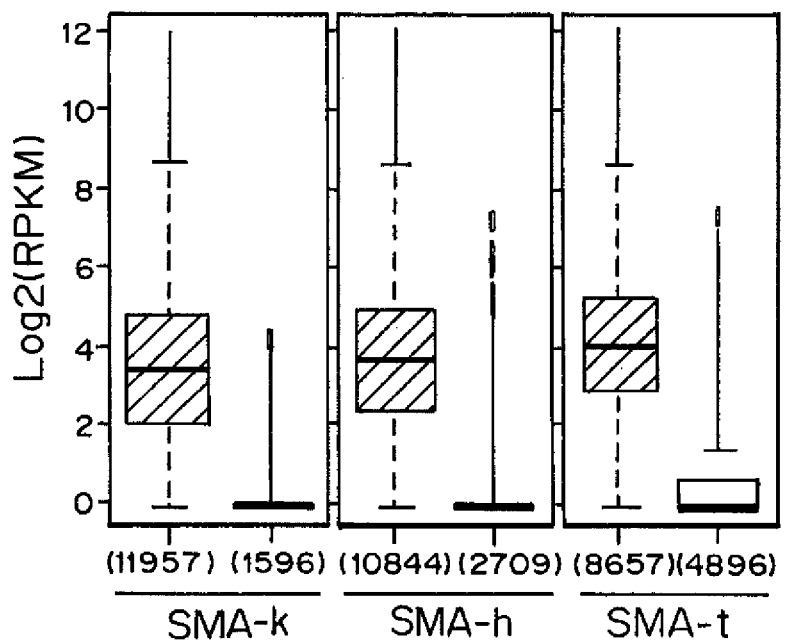

Next, the analysis of single cell transcriptomes using PMA was explored. It is worth noting that recovering signatures for the transcriptome of single cells is highly dependent on cell type. At one extreme, resting lymphocytes have little cytoplasm or RNA, and may be poor candidates for single cell RNA amplification. To demonstrate the utility of PMA for single cells, single K562 erythroleukemic cells were manually isolated from suspension culture. Using ¼ of a lane of multiplex sequencing (75 nucleodtides PE reads), approximately 5000 transcripts were detected and the more abundant genes were well represented with coverage of most or all exons. Higher level expressed genes are more consistently detected (FIGS. 3A (PMA) and 3B (SMA)). The RefSeq genes with RPKM >0.1 counts are considered as detected, and RPKM <0.1 counts are considered as missed. With STD used as the control, the gene numbers detected or missed are listed as in the x axis. The $\log_2$(RPKM) is used as the y axis. The box plot was generated with RNA-seq reads assembled by Cufflinks, with the RefSeq GTF file as a reference annotation. For all these amplicons, the Wilcoxon test revealed a significance for the RPKM between the genes detected vs. missed (P<2.2E-16). Many less abundant genes were either not detected or incompletely represented at the depth of sequencing used.

Figure 4:
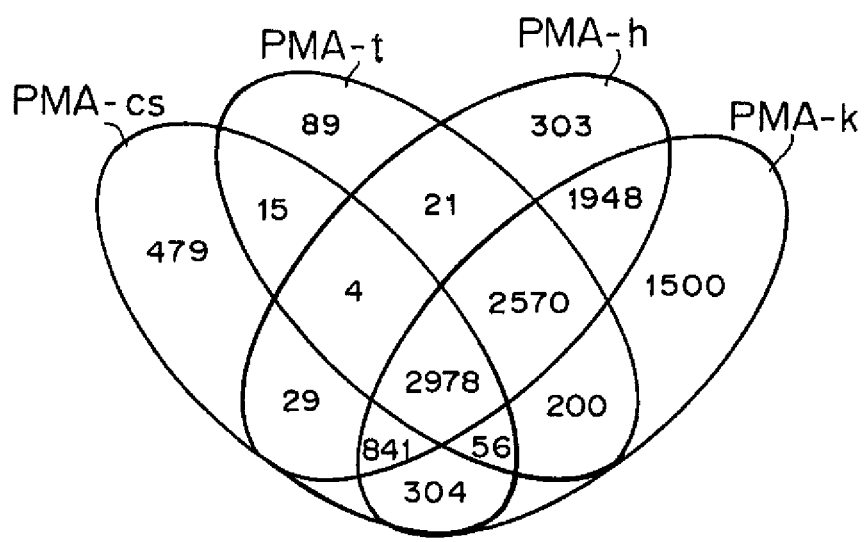
FIG. 4 is a Venn diagram showing RNAs for PMA-cs versus PMA-k, PMA-h, and PMA-t for gene detection (cs represent single cell sample, k refers to sample of 1000-cells, h refers to 100-cells, and t refers to 10-cells). All RPK>0.1 counts are considered.

In one analysis, mapping distribution of sequencing reads from PMA of a single K562 cell (PMA-cs) isoforms or CDS/UTRs were compared with 1,000-cell PMA (PMA-k). PMA-cs totally covered 5,277 genes (each with at least one transcript), independent exons, introns, and other signals. This single cell PMA sequencing also showed more unknown transcripts, and unannotated transcripts than did amplicons from 1000-cell equivalent diluted RNA. However, the mapped genes overall are similar to those when more cells were amplified. The Venn diagram in FIG. 4 shows RNAs for PMA-cs versus PMA-k, PMA-h, and PMA-t for gene detection. All RPKM >0.1 counts are considered. RNA-seq reads were assembled by Cufflinks with the RefSeq GTF file as a reference annotation.

The same analyses was applied to a set of single murine dorsal root ganglion cell bodies, each individually harvested by suction applied by a micropipette from an intact ganglion whose cells were loosened from their cellular neighbors by prior topical application of collagenase (Ma, et al., *J Neurosci Methods.* 191(1):60-65 (2010)), a similar level of transcripts were also detected and the results defined the cell type specificity of the transcriptome of these neurons. The cDNA from these neurons was amplified by PMA after each neuron had been functionally classified as nociceptive by its action potential responses, electrophysiologically recorded in vivo, to noxious chemical, thermal or mechanical stimuli delivered to its cutaneous receptive field (Ma, et al., *J*

*Neurophysiol.* 107(1):357-363 (2012)). In addition, the application of SMA to single cells is also promising.

In addition to the technical considerations, there is another level of complexity in evaluating the transcriptome of single cells, especially cells substantially smaller than oocytes or early blastocysts. The mRNA has a relatively short half life and transcription may occur in bursts (Suter, et al., *Curr Opin Cell Biol.* 23(6):657-662 (2011), Hager, et al., *Mol Cell.* 35(6):741-753 (2009), Voss, et al., *Cell.* 146(4):544-554 (2011)). Thus at any one time, the mRNA content of a cell may be an incomplete representation of the total transcriptome during the cell cycle, as demonstrated here for single K562 cells. The contribution of this stochasticity to the results of single cell analysis is difficult to evaluate. This phenomenon indicates that it is best to evaluate the transcriptome from several cells as nearly identical in nature, as possible, such as cell cycle stage synchronized, in order to get the full signature of the transcriptome of a single cell type (Wang, et al., *Trends Biotechnol.* 28(6):281-290 (2010)).

Collectively, the Examples herein demonstrate that rather similar overall results can be obtained for cDNA profiling from LQ cells or even single cells by either of the two amplification procedures described. Importantly, these methods can provide a relatively uniform representation of the full-length of even very long cDNAs. At the single cell level, coverage is incomplete but adequate for the detection of the more abundant mRNA species, and could be used to evaluate their relative use of different splice isoforms, as well as the detection of unannotated transcripts. In summary, these approaches offer considerable promise for applications in studies of a range of subjects, including development, nervous system structure, and normal and pathologic responses of the human immune system.

We claim:

1. A method of preparing cDNA from one or more cells, comprising sequentially
    (a) preparing single stranded cDNA from cellular RNA of the one or more cells by a reverse transcription (RT) reaction comprising
        (1) denaturing the cellular RNA;
        (2) annealing one or more RT primers to the cellular RNA; and
        (3) extending the RT primers to form the cDNA;
    wherein the sequences of cellular RNA consist of RNA sequences from the one or more cells;
    (b) preparing double stranded cDNA by second strand synthesis of the single stranded cDNA;
    (c) circularizing the double stranded cDNA; and
    (d) amplifying the circularized double stranded cDNA by a multiple displacement amplification (MDA) reaction comprising annealing one or more MDA primers to the cDNA and extending the MDA primers with a phi29 DNA polymerase to form a cDNA library representative of the mRNA transcriptome or whole RNA transcriptome of the one or more cells; wherein steps (a) through (c) are carried out in the absence of active DNA endonuclease.

2. The method of claim 1 wherein the reverse transcription, the second strand synthesis, the circularization, the amplification, or any combination thereof are carried out substantially free from contamination of cellular genomic DNA.

3. The method of claim 2 wherein the one or more cells comprise a plasma membrane and a nucleus with a nuclear membrane, and the method further comprises preparing the cellular RNA for reverse transcription by lysing the one or more cells under conditions that disrupt the plasma membrane but leave the nuclear membrane intact.

4. The method of claim 2 further comprising substantially purifying the cellular RNA from the cellular genomic DNA prior to reverse transcription.

5. The method of claim 1 wherein the one or more RT primers are single stranded oligonucleotides selected from the group consisting of
    (i) 5'-phosphorylated oligo(dT);
    (ii) 5'-phosphorylated oligo(dT) with a 3' anchor nucleotide that is not thymidine;
    (iii) a mixture of random primers; and
    (iv) any combination thereof.

6. The method of claim 1 wherein the MDA primer is a mixture of random primers.

7. The method of claim 1 wherein the whole MDA reaction is carried out for at least 8 hours at a temperature between about 26° C. and about 40° C. and in the presence of Tre [d-(+)-trehalose dehydrate] at a concentration of 0.2-1 M.

8. The method of claim 1 further comprising (e) fragmentation of the cDNA.

9. The method of claim 1 wherein the yield of the cDNA is at least 2 µg when the one or more cells is no greater than $5 \times 10^5$ cells.

10. The method of claim 1 further comprising ligating adaptor oligonucleotides to the amplified cDNA to facilitate sequencing.

11. The method of claim 3 further comprising substantially purifying the cellular RNA from the cellular genomic DNA prior to reverse transcription.

12. The method of claim 5 wherein the one or more RT primers are single stranded oligonucleotides comprising 5'-phosphorylated oligo(dT) and a mixture of random primers.

13. The method of claim 8 further comprising ligating adaptor oligonucleotides to the fragmented cDNA to facilitate sequencing.

14. The method of claim 1, wherein the one or more cells are eukaryotic cells.

15. The method of claim 11, wherein the RNA is substantially purified from the cellular genomic DNA by harvesting cytoplasmic RNA from the cellular genomic DNA in the cell lysate.

16. The method of claim 2 comprising substantially isolating the cellular genomic DNA from the cellular RNA prior to reverse transcription.

17. The method of claim 1 wherein steps (a) through (c) do not comprise a template switching mechanism.

18. The method of claim 17, wherein step (c) is carried out under conditions that drive intramolecular circularization and reduces linear concatemers.

19. The method of claim 1, wherein the cDNA library comprises a uniform representation of the full-length cellular RNA expressed by the one or more cells.

20. The method of claim 1, wherein the one or more cells is less than 100,000 cells.

* * * * *